(12) United States Patent
Renhowe et al.

(10) Patent No.: US 7,138,409 B2
(45) Date of Patent: *Nov. 21, 2006

(54) HETEROCYCLIC COMPOUNDS

(75) Inventors: Paul A. Renhowe, Danville, CA (US); Timothy Machajewski, Martinez, CA (US); Cynthia Shafer, Moraga, CA (US); Mary Ellen Wernette Hammond, Castro Valley, CA (US); Sabina Pecchi, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 266 days.

This patent is subject to a terminal disclaimer.

(21) Appl. No.: 10/823,995

(22) Filed: Apr. 14, 2004

(65) Prior Publication Data

US 2005/0137188 A1    Jun. 23, 2005

Related U.S. Application Data

(60) Continuation of application No. 10/452,786, filed on Jun. 2, 2003, now Pat. No. 6,759,417, which is a division of application No. 09/943,382, filed on Aug. 30, 2001, now Pat. No. 6,756,383.

(60) Provisional application No. 60/231,829, filed on Sep. 1, 2000.

(51) Int. Cl.
- C07D 413/14 (2006.01)
- C07D 471/02 (2006.01)
- A61K 31/436 (2006.01)
- A61K 31/4375 (2006.01)

(52) U.S. Cl. ............ 514/302; 514/253.04; 514/254.06; 514/301; 544/111; 544/242; 546/123

(58) Field of Classification Search ................. 514/301, 514/302, 253.04, 254.06; 546/123; 544/111, 544/242

See application file for complete search history.

(56) References Cited

U.S. PATENT DOCUMENTS

| | | |
|---|---|---|
| 4,882,342 A | 11/1989 | Von der Saal et al. |
| 5,073,492 A | 12/1991 | Chen et al. |
| 5,414,088 A | 5/1995 | Von der Saal et al. |
| 5,585,380 A | 12/1996 | Bianco et al. |
| 5,646,153 A | 7/1997 | Spada et al. |
| 5,710,158 A | 1/1998 | Myers et al. |
| 5,763,441 A | 6/1998 | App et al. |
| 5,792,771 A | 8/1998 | App et al. |
| 5,801,212 A | 9/1998 | Okamoto et al. |
| 5,855,866 A | 1/1999 | Thorpe et al. |
| RE36,256 E | 7/1999 | Spada et al. |
| 5,942,385 A | 8/1999 | Hirth |
| 5,981,569 A | 11/1999 | App et al. |
| 6,057,320 A | 5/2000 | Spada et al. |
| 6,258,951 B1 | 7/2001 | Lohmann et al. |
| 6,303,600 B1 | 10/2001 | Cox et al. |
| 6,306,874 B1 | 10/2001 | Fraley et al. |
| 6,313,138 B1 | 11/2001 | Fraley et al. |
| RE37,650 E | 4/2002 | Myers et al. |
| 6,420,382 B1 | 7/2002 | Fraley et al. |
| 6,479,512 B1 | 11/2002 | Fraley et al. |
| 6,605,617 B1 | 8/2003 | Renhowe et al. |
| 6,762,194 B1 | 7/2004 | Renhowe et al. |
| 6,774,327 B1 | 8/2004 | Wong |
| 6,800,760 B1 | 10/2004 | Renhowe et al. |
| 2002/0103230 A1 | 8/2002 | Renhowe et al. |
| 2003/0028018 A1 | 2/2003 | Renhowe et al. |
| 2003/0207883 A1 | 11/2003 | Renhowe et al. |
| 2004/0002518 A1 | 1/2004 | Renhowe et al. |

FOREIGN PATENT DOCUMENTS

| | | |
|---|---|---|
| DE | 2363459 | 6/1975 |
| DE | 3634066 A1 | 7/1986 |
| DE | 19841985 | 3/2000 |
| EP | 0290153 | 11/1988 |
| EP | 0 509 717 | 4/1992 |
| EP | 0 508 800 | 10/1992 |

(Continued)

OTHER PUBLICATIONS

Zetter, B. R., "Angiogenesis and Tumor Metastasis," Annu. Rev. Med., 1998, vol. 49, pp. 407-424; published by Annual Review Inc.

(Continued)

*Primary Examiner*—Zinna N. Davis
(74) *Attorney, Agent, or Firm*—Young J. Suh; Joseph P. Meara; Alisa A. Harbin

(57) ABSTRACT

Organic compounds having the structural formula I are provided where the variables have the values described herein and $R^1$ and $R^2$ join together to form a 6 membered substituted or unsubstituted ring including at least one O, N, or S atom, and Z is an O, S, NH or NR group.

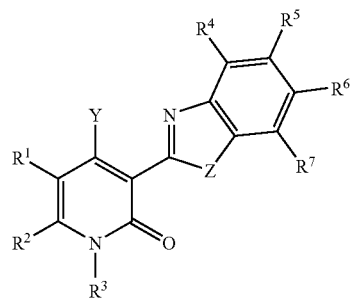

Pharmaceutical formulations include the organic compound or a pharmaceutically acceptable salt thereof and a pharmaceutically acceptable carrier.

19 Claims, No Drawings

FOREIGN PATENT DOCUMENTS

| | | |
|---|---|---|
| EP | 0 747 771 | 12/1996 |
| EP | 0 797 376 | 9/1997 |
| EP | 0 290 153 | 11/1998 |
| EP | 1 086 705 | 3/2001 |
| JP | 6-9952 | 1/1994 |
| JP | 7-43896 | 2/1995 |
| JP | 8-29973 | 2/1996 |
| JP | 63-258903 | 10/1998 |
| WO | 92/18483 | 10/1992 |
| WO | 92/20642 | 11/1992 |
| WO | 95/15758 | 6/1995 |
| WO | 95/18801 | 7/1995 |
| WO | 97/03069 | 1/1997 |
| WO | 97/34876 | 9/1997 |
| WO | 97/48694 | 12/1997 |
| WO | 98/13350 | 4/1998 |
| WO | 99/10349 | 3/1999 |
| WO | 99/50263 | 10/1999 |
| WO | 99/65897 | 12/1999 |
| WO | WO 00/00481 | 1/2000 |
| WO | WO 00/03990 | 1/2000 |
| WO | WO 00/20400 | 4/2000 |
| WO | 00/27379 | 5/2000 |
| WO | 01/02369 | 1/2001 |
| WO | 01/28993 | 4/2001 |
| WO | 01/29025 | 4/2001 |
| WO | WO 01/28993 | 4/2001 |
| WO | 01/52904 | 7/2001 |
| WO | 01/55114 | 8/2001 |
| WO | 01/62251 | 8/2001 |
| WO | 01/62252 | 8/2001 |
| WO | WO 02/18383 | 3/2002 |
| WO | WO 02/22598 | 3/2002 |
| WO | 02/32861 | 4/2002 |
| WO | WO 03/087095 | 10/2003 |
| WO | WO 2004/018419 | 3/2004 |
| WO | WO 2004/030620 | 4/2004 |
| WO | WO 2004/043389 | 5/2004 |
| WO | WO 2004/087153 | 10/2004 |
| WO | WO 2005/046589 | 5/2005 |
| WO | WO 2005/053692 | 6/2005 |

OTHER PUBLICATIONS

MSNBC News Services, "Mixed results on new cancer drug," Nov. 9, 2000.

Gura, T., "Systems for Identifying New Drugs Are Often Faulty," *Science*, 1997, vol. 278, pp. 1041-1042.

Dermer, G. B., "Another Anniversary for the War on Cancer," *Biotechnology*, 1994, vol. 12, p. 320.

Freshney, R. I., *Culture of Animal Cells—A Manual of Basic Technique*, 1983, pp. 1-4; published by Alan R. Liss, Inc.

Angiogenesis Foundation, "New Study Shows That Acute Myeloid Leukemia is Angiogenesis-Dependent," Jan. 4, 2000; www.angio.org/newsandviews/ archive2000/jan_4_2000.html.

Hussong, J. W. et al., "Evidence of increased angiogenesis in acute myeloid leukemia," *Blood*, 2000, vol. 95(1), pp. 309-313; The American Society of Hematology.

Kerbel, R. S., "Tumor Angiogenesis: Past, Present and Near Future," *Carcinogenesis*, 2000, vol. 21(3), pp. 505-515; Oxford University Press.

Lundberg, L. G. et al., "Bone Marrow in Polycythemia Vera, Chronic Myelocytic Leukemia, and Myelofibrosis Has an Increased Vascularity," *American Journal of Pathology*, 2000, vol. 157(1), pp. 15-19.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Gruber, G. et al., "Basic Fibroblast Growth Factor is Expressed in CD19/CD11c-Positive Cells in Hairy Cell Leukemia," *Blood*, 1999, vol. 94(3), pp. 1077-1085.

International Search Report for PCT/US2005/005316 dated Nov. 28, 2005.

Aprelikova, O., et al., "FLT4, a novel Class III Receptor Tyrosine Kinase in chromosome 5q33-qter1," *Cancer Res.*, vol. 52, pp. 746-748, Feb. 1, 1992, published by The American Association for Cancer Research, Stanford University Libraries High Wire Press, California, United States of America.

Carmeliet, P. et al., "Angiogenesis in Cancer and Other Diseases," *Nature*, 407, pp. 249-257 (2000).

Connolly, D., et al., "Human Vascular Permeability Factor," *J. Biol. Chem.*, vol. 264, pp. 20017-20024, 1989, published by The American Society For Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," *J. Clin. Invest.*, vol. 84, pp. 1470-1478, Nov. 1989, published by The American Society for Clinical Investigation, Inc., Stanford University Libraries'High Wire Press, California, United States of America.

DeVries, C., et al., "The fms-Like Tyrosine Kinase, a Receptor for Vascular Endothelial Growth Factor," *Science*, vol. 255, pp. 989-991, Feb. 21, 1992, published by The American Society for the Advancement of Science, Stanford University Libraries'High Wire Press, California, United States of America.

Ferrara, N., et al., "The Biology of Vascular Endothelial Growth Factor," *Endocrinol. Rev.*, vol. 18, No. 1, pp. 4-25, 1997, published by The Endocrine Society, Stanford University Libraries' High Wire Press, California, United States of America.

Folkman, J., "Fighting Cancer by Attacking Its Blood Supply," *Scientific American*, vol. 275, pp. 150-154, Sep. 1996, published by Scientific American, Inc., New York, New York, United States of America.

Hennequin, L. F., et al., Design and Structure—Activity Relationship of a New Class of Potent VEGF Receptor Tyrosine Kinase Inhibitors,: *J. Med. Chem.*, vol. 42, No. 26, pp. 5369-5389, 1999; published by American Chemical Society, Washington, D.C.

Leung, D., et al., "Vascular Endothelial Growth Factor Is a Secreted Angiogenic Mitogen," *Science*, vol. 246, pp. 1306-1309, Dec. 8, 1989, published by The American Society for the Advancement of Science, Stanford University Libraries' High Wire Press, California, United States of America.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Maguire, M.P., et a., "A New Series of PDGF Receptor Tyrosine Kinase Inhibitors: 3-Substituted Quinoline Derivatives," *J. Med. Chem.*, vol. 37, No. 14, pp. 2129-2137, 1994; published by American Chemical Society, Washington, D.C.

Matei, S., et al., "Condensation of ethyl 2-benzimidazoleacetate with carbonyl compounds," *Rev. Chim.*, vol. 33, No. 6, pp. 527-530, 1989, published by the Central Institute of Chemistry, Bucharest, Romania.

Mustonen, T., et al., "Endothelial Receptor Tyrosine Kinases Involved in Angiogenesis," *J. Cell Biology*, vol. 129, No. 4, pp. 895-898, May 1995, published by The Rockfeller University Press, New York, New York, United States of America.

Plouet, J., et al., "Isolation and characterization of a newly identified endothelial cell mitogen produced by AtT-20 cells," *EMBO J.*, vol. 8, No. 12, pp. 3801-3806, 1989, published by IRL Press.

Quinn, T., et al., "Fetal liver kinase 1 is a receptor for vascular endothelial growth factor and is selectively expressed in vascular endothelium," *Proc. Natl. Acad. Sci. USA*, vol. 90, pp. 7533-7537, Aug. 1993.

Shibuya, M., et al., "Nucleotide sequence and expression of a novel human receptor-type tyrosine kinase gene (flt) closely related to the fms family," *Oncogene*, vol. 5, pp. 519-524, 1990, published by Macmillan Press Ltd., Stockton Press Company, Great Britain.

Stover, D. R., "Recent advances in protein kinase inhibition: Current molecular scaffolds used for inhibitor synthesis," *Current Opinion in Drug Discovery & Development*, vol. 2, No. 4, 274-285, 1999; published by PharmaPress Ltd., London, United Kingdom.

Terman, B., et al., "Identification of a new endothelial cell growth factor receptor tyrosine kinase," *Oncogene*, vol. 6, pp. 1677-1683, 1991, published by Macmillan Press Ltd., Stockton Press Company, Great Britain.

Ukrainets, I., "Effective Synthesis of 3-(Benzimidazol-2-yl)-4-Hydroxy-2-Oxo-1,2-Dihydroquinolines," *Tet. Lett.*, vol. 36, No. 42, pp. 7747-7748, 1995, published by Elsevier Science Ltd., Great Britain.

Ukrainets, I., et al., "2-Carbethoxymethyl-4H-3,1-Benzoxazin-4-One. 3. *Condensation of o-Phenylenediamine," pp. 198-200, translated from *Khimiya Geterotsiklicheskikh Soedinii*, No. 2, pp. 239-241, Feb. 1992, published by Plenum Publ. Corp., London, Great Britain.

Ukrainets, I., et al., "4-Hydroxy-2-Quinolones 7.* Synthesis and Biological Properties of 1-R-3-(2-Benzimidazolyl)-4-Hydroxy-2Quinolones," pp. 92-94, translated from *Khimiya Geterotsiklicheskikh Soedinii*, No. 1, pp. 105-108, Jan. 1993, published by Plenum Publ. Corp. London, Great Britain.

Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antithyroid Activity of Thio Analogs of 1H-2-OXO-3-(2-Benzimidazolyl)-4-HydroxyQuinoline," *Chem. Heterocyclic Comp.*, vol. 33, No. 5, pp. 600-604, 1997, published by Kluwer Academic Publishers, London, Great Britain.

Ullrich, A., et al., "Signal Transduction by Receptors with Tyrosine Kinase Activity," *Cell*, vol. 61, pp. 203-212, Apr. 20, 1990, published by Cell Press, Cambridge, Massachusetts, United States of America.

van der Geer, P., et al., "Receptor Protein-Tyrosine Kinases and Their Signal Transduction Pathways," *Annu. Rev. Cell Biol.*, vol. 10, pp. 251-337, 1994, published by Annual Reviews, Inc., Palo Alto, California, United States of America.

Salmon, S. E. et al., *Basic & Clinical Pharmacology, Seventh Edition*, edited by B. Katzung, Appleton & Lange, pp. 29, 881-884 (1998).

Milauer, B. et al., "Glioblastoma Growth Inhibited In Vivo by a Dominant-Negative Flk-1 Mutant," *Nature*, vol. 367, pp. 576-579 (1994); published by Nature Publishing Group.

Pinedo, H. M. et al., "Translational Research: The Role of VEGF in Tumor Angiogenesis," *The Oncologist 2000*, vol. 5 (suppl. 1), pp. 1-2 (2000).

McMahon, G., "VEGF Receptor Signaling in Tumor Angiogenesis," *The Oncologist 2000*, vol. 5 (suppl. 1), pp. 3-10 (2000).

Cecil, Textbook of Medicine, 21$^{st}$ Edition (2000), Goldman & Bennett (Editors), W.B. Saunders Company (Publisher), Chapter 198, pp. 1060-1074).

U.S. Appl. No. 10/644,055, filed Aug. 2003, Barsanti et al.

U.S. Appl. No. 10/839,793, filed May 2004, Barsanti et al.

U.S. Appl. No. 10/982,543, filed Nov. 2004, Cai et al.

European Search Report dated Feb. 28, 2006 for EP 05017665.0.

Ukrainets, et al., "Effective Synthesis of 3-(Benzimidazol-2-yl)-4-Hydroxy-2-Oxo-1,2-Dihydroquinolines," Tetrahedron Letters, vol. 36, No. 42, 1995, pp. 7747-7748.

Carla Heise, et al., "In vivo Preclinical Evaluation of Tyrosine Kinase Inhibitors with Potent Effects on Tumor Angiogenesis, Growth and Metastasis," Abstract and presentation material for a presentation at the American Association for Cancer Research meeting held in Apr. 2002.

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: 6X-His tag

<400> SEQUENCE: 1

His His His His His His
 1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 2

Gly Gly Gly Gly Gln Asp Gly Lys Asp Tyr Ile Val Leu Pro Ile
 1               5                  10                  15

HETEROCYCLIC COMPOUNDS

CROSS-REFERENCES TO RELATED APPLICATIONS

This application is a continuation of and claims priority to U.S. Ser. No. 10/452,786, filed on Jun. 2, 2003, now U.S. Pat. No. 6,759,417, which is a divisional of and claims priority to U.S. Ser. No. 09/943,382, filed on Aug. 30, 2001, now U.S. Pat. No. 6,756,383, which claims priority to U.S. Provisional Application No. 60/231,829 filed on Sep. 1, 2000, now abandoned, the entire disclosures each of which are incorporated herein by reference and for all purposes as if fully set forth herein.

FIELD OF THE INVENTION

This invention pertains generally to treating diseases characterized by angiogenesis including cancer. More specifically, the invention described herein pertains to treating diseases characterized by activity of vascular endothelial growth factor receptor tyrosine kinases. The present invention provides small molecule inhibitors of vascular endothelial growth factor receptor tyrosine kinase, pharmaceutical formulations containing such inhibitors, methods of treating patients with such pharmaceutical formulations, and methods of preparing such pharmaceutical formulations and inhibitors.

BACKGROUND OF THE INVENTION

Capillaries reach into almost all tissues of the human body and supply tissues with oxygen and nutrients as well as removing waste products. Under typical conditions, the endothelial cells lining the capillaries do not divide, and capillaries, therefore, do not normally increase in number or size in a human adult. Under certain normal conditions, however, such as when a tissue is damaged, or during certain parts of the menstrual cycle, the capillaries begin to proliferate rapidly. This process of forming new capillaries from pre-existing blood vessels is known as angiogenesis or neovascularization. See Folkman, J. Scientific American 275, 150–154 (1996). Angiogenesis during wound healing is an example of pathophysiological neovascularization during adult life. During wound healing, the additional capillaries provide a supply of oxygen and nutrients, promote granulation tissue, and aid in waste removal. After termination of the healing process, the capillaries normally regress. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. Thus, inhibition of angiogenesis is expected to retard or halt the growth of cancer cells.

Receptor tyrosine kinases (RTKs) are transmembrane polypeptides that regulate developmental cell growth and differentiation and remodeling and regeneration of adult tissues. Mustonen, T. et al., J. Cell Biology 129, 895–898 (1995); van der Geer, P. et al. Ann Rev. Cell Biol. 10, 251–337 (1994). Polypeptide ligands known as growth factors, or cytokines, are known to activate RTKs. Signaling of RTKs involves ligand binding and a shift in conformation in the external domain of the receptor resulting in its dimerization. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999); Ullrich, A. et al., Cell 61, 203–212 (1990). Binding of the ligand to the RTK results in receptor trans-phosphorylation at specific tyrosine residues and subsequent activation of the catalytic domains for the phosphorylation of cytoplasmic substrates. Id.

Two subfamilies of RTKs are specific to the vascular endothelium. These include the vascular endothelial growth factor (VEGF) subfamily and the Tie receptor subfamily. Class III RTKs include VEGFR-1, VEGFR-2, and VEGFR-3. Shibuya, M. et al., Oncogene 5, 519–525 (1990); Terman, B. et al., Oncogene 6, 1677–1683 (1991); Aprelikova, O. et al., Cancer Res. 52, 746–748 (1992).

Members of the VEGF subfamily have been described as being able to induce vascular permeability and endothelial cell proliferation and further identified as a major inducer of angiogenesis and vasculogenesis. Ferrara, N. et al., Endocrinol. Rev. 18, 4–25 (1997). VEGF is known to specifically bind to RTKs including VEGFR-1 and VEGFR-2. DeVries, C. et al., Science 255, 989–991 (1992); Quinn, T. et al., Proc. Natl. Acad. Sci. 90, 7533–7537 (1993). VEGF stimulates the migration and proliferation of endothelial cells and induces angiogenesis both in vitro and in vivo. Connolly, D. et al., J. Biol. Chem. 264, 20017–20024 (1989); Connolly, D. et al., J. Clin. Invest. 84, 1470–1478 (1989); Ferrara, N. et al., Endocrino. Rew. 18, 4–25 (1997); Leung, D. et al., Science 246, 1306–1309 (1989); Plouet, J. et al., EMBO J 8, 3801–3806 (1989).

Because angiogenesis is known to be critical to the growth of cancer and to be controlled by VEGF and VEGF-RTK, substantial efforts have been undertaken to develop therapeutics that are antagonists of VEGF-RTK to thereby inhibit or retard angiogenesis, and hopefully interfere or stop tumor proliferation.

A wide variety of chemical compounds and compositions have been reported as having activity against one of more the VEGF-RTKs. Examples include quinoline derivatives such as described in WO 98/13350, aminonicotinamide derivatives (see, e.g., WO 01/55114), antisense compounds (see, e.g., WO 01/52904), peptidomimetics (see, e.g., WO 01/52875), quinazoline derivatives (see, e.g., U.S. Pat. No. 6,258,951) monoclonal antibodies (see, e.g., EP 1 086 705 A1), various 5, 10, 15, 20-tetraaryl-porphyrins and 5, 10, 15-triaryl-corroles (see, e.g., WO 00/27379), heterocyclic alkanesulfonic and alkane carboxylic acid derivatives (see, e.g., DE19841985), oxindolylquinazoline derivatives (see, e.g., WO 99/10349), 1,4-diazaanthracine derivatives (see, e.g., U.S. Pat. No. 5,763,441), and cinnoline derivatives (see, e.g., WO 97/34876), and various indazole compounds (see e.g., WO 01/02369 and WO 01/02369).

Various indolyl-substituted compounds have recently been disclosed in WO 01/29025, and various benzimidazolyl compounds have recently been disclosed in WO 01/28993. These compounds are reportedly capable of inhibiting, modulating, and/or regulating signal transduction of both receptor-type and non-receptor tyrosine kinases. Some of the disclosed compounds contain a quinolone fragment bonded to the indolyl or benzimidazolyl group.

The synthesis of 4-hydroxy quinolone and 4-hydroxy quinoline derivatives is disclosed in a number of references. For example, Ukrainets et al. have disclosed the synthesis of 3-(Benzimidazol-2-yl)-4-hydroxy-2-oxo-1,2-dihydroquinoline. Ukrainets, I. et al., Tet. Lett. 42, 7747–7748 (1995); Ukrainets, I. et al., Khimiya Geterotsiklicheskikh Soedinii, 2, 239–241(1992). Ukrainets has also disclosed the synthesis, anticonvulsive and antithyroid activity of other 4-hydroxyquinolones and thio analogs such as 1H-2-oxo-3-(2- benzimidazolyl)-4-hyrdoxyquinoline. Ukrainets, I. et al., Khimiya Geterotsiklicheskikh Soedinii, 1, 105–108 (1993); Ukrainets, I. et al., Khimiya Geterotsiklicheskikh Soedinii, 8, 1105–1108 (1993); Ukrainets, I. et al., Chem. Heterocyclic Comp. 33, 600–604, (1997).

The synthesis of various quinoline derivatives is disclosed in WO 97/48694. These compounds are disclosed as capable of binding to nuclear hormone receptors and being useful for stimulating osteoblast proliferation and bone growth. The compounds are also disclosed as being useful in the treatment or prevention of diseases associated with nuclear hormone receptor families.

Various quinoline derivatives in which the benzene ring of the quinolone is substituted with a sulfur group are disclosed in WO 92/18483. These compounds are disclosed as being useful in pharmaceutical formulations and as medicaments.

Quinolone and coumarin derivatives have been disclosed as having use in a variety of applications unrelated to medicine and pharmaceutical formulations. References that describe the preparation of quinolone derivatives for use in photopolymerizable compositions or for luminescent properties include: U.S. Pat. No. 5,801,212 issued to Okamoto et al.; JP 8-29973; JP 7-43896; JP 6-9952; JP 63-258903; EP 797376; and DE 23 63 459.

Despite the exploration of a variety of chemistries to provide VEGF-RTK-antagonist therapies, a continuing need exists for compounds that inhibit the proliferation of capillaries, inhibit the growth of tumors, and/or inhibit vascular endothelial growth factor receptor tyrosine kinase and pharmaceutical formulations that contain such compounds. A need also exists for methods for administering such compounds and pharmaceutical formulations to patients in need thereof.

SUMMARY OF THE INVENTION

The present invention provides compounds, pharmaceutical formulations including the compounds, methods of preparing the pharmaceutical formulations, and methods of treating patients with the pharmaceutical formulations and compounds.

The present invention provides compounds having the structure I. The invention also provides tautomers of the compounds, pharmaceutically acceptable salts of the compounds, and pharmaceutically acceptable salts of the tautomers. Structure I has the following formula:

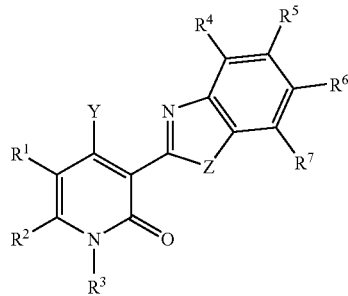

I where:

Y is selected from —OH, —OR$^8$ groups, —SH, —SR$^9$ groups, —NR$^{10}$R$^{11}$ groups, —CN, —C(=O)—R$^{12}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

Z is O, S, or a NR$^{13}$ group;

R$^1$ and R$^2$ join to form a 5 to 7 membered substituted or unsubstituted ring including at least one O, N, or S atom;

R$^3$ and R$^{13}$ may be the same or different and are selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted and unsubstituted heterocyclylamino groups, substituted and unsubstituted diheterocyclylamino groups, substituted and unsubstituted (alkyl)(heterocyclyl)amino groups, substituted and unsubstituted (aryl)(heterocyclyl)amino groups, substituted and unsubstituted heterocylyloxy groups, substituted or unsubstituted alkyl groups, substituted or unsubstituted aryl groups, —C(=O)H, —C(=O)-alkyl groups, or —C(=O)-aryl groups;

R$^4$, R$^5$, R$^6$, and R$^7$ may be the same or different and are independently selected from H, Cl, Br, F, I, —NO$_2$, —CN, —OH, —OR$^{14}$ groups, —NR$^{15}$R$^{16}$ groups, —C(=O)R$^{17}$ groups, —SH, —SR$^{18}$ groups, —S(=O)R$^{19}$ groups, S(=O)$_2$ R$^{20}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl) aminoalkyl groups, substituted or unsubstituted heterocyclylalkyl groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

R$^8$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O) NH(alkyl) groups, —C(=O)NH(aryl) groups, —C(=O)N (alkyl)$_2$ groups, —C(=O)N(aryl)$_2$ groups, —C(=O)N (alkyl)(aryl) groups, —NH$_2$, —NH(alkyl) groups, —NH (aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

$R^9$ and $R^{18}$ may be the same or different and are independently selected from substituted or unsubstituted alkyl groups, or substituted or unsubstituted aryl groups;

$R^{10}$ is selected from H, substituted or unsubstituted alkyl groups, substituted or unsubstituted aryl groups, or substituted or unsubstituted heterocyclyl groups;

$R^{11}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{12}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups;

$R^{14}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)-heterocyclyl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)NH-heterocyclyl groups, —C(=O)N-(heterocyclyl)$_2$ groups, —C(=O)N(alkyl)(heterocyclyl) groups, —C(=O)N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups;

$R^{15}$ is selected from H, substituted or unsubstituted alkyl groups, substituted or unsubstituted aryl groups, or substituted or unsubstituted heterocyclyl groups;

$R^{16}$ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; and $R^{17}$, $R^{19}$, and $R^{20}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, —OH, substituted and unsubstituted alkoxy groups, substituted and unsubstituted heterocyclyl groups, substituted and unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups.

Preferred compounds having the structure I are provided where Y is selected from —OH, —OR$^8$ groups, or —NR$^{10}$R$^{11}$ groups, or more preferably is a —NR$^{10}$R$^{11}$ group.

Still other preferred compounds having the structure I are provided in which Z is an NR$^{13}$ group and the rest of the compound is consistent with any of the above-described compounds.

In still other preferred compounds of structure I, $R^4$ and $R^7$ are hydrogen, $R^6$ and $R^7$ are selected from hydrogen or an alkyl group having from 1 to 4 carbon atoms, and the rest of the compound is consistent with any of the above-described compounds.

Still other compounds having the formula of structure I are provided in which $R^5$ or $R^6$ is an —OR$^{14}$ group and $R^{14}$ is an alkyl, aryl, heterocyclyl, or heterocyclylalkyl group and the rest of the molecule is consistent with any of the above-described compounds.

In still further preferred compounds having the formula of structure I, $R^5$ or $R^6$ is a —OCH$_2$(CH$_2$)$_q$(heterocyclyl) group where q is 0, 1, 2, 3, or 4 and the rest of the compound is consistent with any of the above-described compounds.

Other preferred compounds having the structure I are provided in which R$^{17}$ is selected from substituted or unsubstituted alkyl groups, substituted or unsubstituted aryl groups, —NH$_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, or N-containing heterocycles, and the N-containing heterocycles are bonded to the carbonyl carbon of the —C(=O)—R$^{17}$ group through either a nitrogen atom or a carbon atom in the rings of the N-containing heterocycles.

The present invention also provides compounds having the structure III. The invention also provides tautomers of the compounds, pharmaceutically acceptable salts of the compounds, and pharmaceutically acceptable salts of the tautomers. Structure III has the following formula:

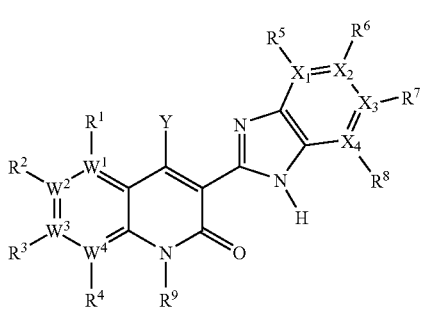

III where:

W$^1$, W$^2$, W$^3$, and W$^4$ are selected from C or N, and at least one of W$^1$, W$^2$, W$^3$, or W$^4$ is N;

X$^1$, X$^2$, X$^3$, and X$^4$ are selected from C or N, and at least one of X$^1$, X$^2$, X$^3$, or X$^4$ is N;

Y is selected from H, —OH, —OR$^{10}$ groups, —SH, —SR$^{11}$ groups, —NR$^{12}$R$^{13}$ groups, —CN, —C(=O)—R$^{14}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocycloxyalkyl groups;

R$^1$, R$^2$, R$^3$, R$^4$, R$^5$, R$^6$, R$^7$, and R$^8$ may be the same or different and are independently selected from H, Cl, Br, F, I, —NO$_2$, —CN, —OH, —OR$^{15}$ groups, —NR$^{16}$R$^{17}$ groups, —C(=O)R$^{18}$ groups, —SH, —SR$^{19}$ groups, —S(=O)R$^{20}$ groups, S(=O)$_2$R$^{19}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl) aminoalkyl groups, substituted or unsubstituted heterocyclylalkyl groups, substituted or unsubstituted aminoalkyl groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups, and R$^1$ is absent or H if W$^1$ is N, R$^2$ is absent or H if W$^2$ is N, R$^3$ is absent or H if W$^3$ is N, R$^4$ is absent or H if W$^4$ is N, R$^5$ is absent or H if X$^1$ is N, R$^6$ is absent or H if X$^2$ is N, R$^7$ is absent or H if X$^3$ is N, and R$^8$ is absent or H if X$^4$ is N;

R$^9$ is selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

R$^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

R$^{10}$ and R$^{19}$ may be the same or different and are independently selected from substituted or unsubstituted alkyl groups, or substituted or unsubstituted aryl groups;

R$^{12}$ is selected from H, substituted or unsubstituted alkyl groups, substituted or unsubstituted aryl groups, or substituted or unsubstituted heterocyclyl groups;

R$^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N (heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{14}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups;

$R^{15}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —(C=O)-heterocyclyl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)NH-heterocyclyl groups, —C(=O)N-(heterocyclyl)$_2$ groups, —C(=O)N(alkyl)(heterocyclyl) groups, —C(=O)N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl) aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups;

$R^{16}$ is selected from H, substituted or unsubstituted alkyl groups, substituted or unsubstituted aryl groups, or substituted or unsubstituted heterocyclyl groups;

$R^{17}$ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O) NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (aryl)(alkyl)aminoalkyl groups, substituted or unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl) (heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (heterocyclyl) (alkyl)aminoalkyl groups, substituted and unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; and $R^{18}$, $R^{20}$, and $R^{21}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl) (aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups.

Preferred compounds having structure III are also provided where one of $W^1$, $W^2$, $W^3$, or $W^4$ is N.

Preferred compounds having structure III are also provided where one of $X^1$, $X^2$, $X^3$, or $X^4$ is N.

Preferred compounds having structure III are also provided where Y is selected from H, —OH, —OR$^{10}$ groups, or —NR$^{12}$R$^{13}$ groups, or more preferably is a —NR$^{12}$R$^{13}$ group.

Still other preferred compounds having structure III are provided where $R^5$ is H, $X^4$ is N, $R^6$ and $R^7$ are selected from H or alkyl groups having from one to four carbon atoms, and the rest of the compound is consistent with any of the above-described compounds.

Still other compounds of structure III are provided in which $R^6$ or $R^7$ is an —OR$^{15}$ group and $R^{15}$ is an alkyl, aryl, heterocyclyl, or heterocyclylalkyl group and the rest of the molecule is consistent with any of the above-described compounds.

In still further preferred compounds of structure III, $R^6$ or $R^7$ is a —OCH$_2$(CH$_2$)$_q$(heterocyclyl) group, q is 0, 1, 2, 3, or 4, and the rest of the compound is consistent with any of the above-described compounds.

Other preferred compounds having the structure III are provided in which $R^{18}$ is selected from substituted or unsubstituted alkyl groups, substituted or unsubstituted aryl groups, —NH$_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl) (alkyl) groups, —N(heterocyclyl)(aryl) groups, —N(heterocyclyl)$_2$ groups, or N-containing heterocycles, and the N-containing heterocycles are bonded to the carbonyl carbon of the —C(=O)—R$^{18}$ group through either a nitrogen atom or a carbon atom in the rings of the N-containing heterocycles.

Pharmaceutical formulations according to the present invention are provided which include any of the compounds described above in combination with a pharmaceutically acceptable carrier.

A method of treating a patient in need of an inhibitor of vascular endothelial growth factor receptor tyrosine kinase is provided which includes administering an effective amount of the pharmaceutical formulation according to the present invention to a patient in need thereof.

Further objects, features and advantages of the invention will be apparent from the following detailed description.

DETAILED DESCRIPTION OF THE INVENTION

The present invention provides novel compounds that act as antagonists of receptor tyrosine kinases, and, more particularly, as inhibitors of bFGF and VEGF-RTK function. The compounds provided herein can be formulated into pharmaceutical formulations that are useful in treating patients with a need for an inhibitor of VEGF-RTK, especially, in particular embodiments, to provide compositions and methods for reducing capillary proliferation and in the treatment of cancer.

The following abbreviations and definitions are used throughout this application:

"VEGF" is an abbreviation that stands for vascular endothelial growth factor.

"RTK" is an abbreviation that stands for receptor tyrosine kinase.

"VEGF-RTK" is an abbreviation that stands for vascular endothelial growth factor receptor tyrosine kinase.

"Flt-1" is an abbreviation that stands for fms-like tyrosine kinase-1, also known as vascular endothelial growth factor receptor-1 or "VEGFR1".

"KDR" is an abbreviation that stands for kinase-insert domain tyrosine kinase, also known as vascular endothelial growth factor receptor-2 or "VEGFR2".

"bFGF" is an abbreviation that stands for basic fibroblast growth factor.

"bFGFR" is an abbreviation that stands for basic fibroblast growth factor receptor.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl and norbornyl and such rings substituted with straight and branched chain alkyl groups as defined above. Thus the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carboN(s) or hydrogeN(s) are replaced by a bond to non-hydrogen and non-carbon atoms such as, but not limited to, a halogen atom in halides such as F, Cl, Br, and I; and oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. One Example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy, or heterocyclyloxy group. Still other substituted alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl group. Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms.

Examples include, but are not limited to —C≡C(H), —C≡C(CH₃), —C≡C(CH₂CH₃), —C(H₂)C≡C(H), —C(H)₂C—C(CH₃), and —C(H)₂C≡C(CH₂CH₃) among others.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH₃) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e. a benzyl group). Thus the phrase includes, but is not limited to, groups such as benzyl, diphenylmethyl, and 1-phenylethyl (—CH(C₆H₅)(CH₃)) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH₂C(=O)(C₆H₅), and —CH₂(2-methylphenyl) among others.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H-tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 0.3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, pyrrole, homopiperazine, oxazolidin-2-one, pyrrolidin-2-one, oxazole, thiazole, isoxazole, furan, and tetrahydrofuran.

The phrase "substituted heterocyclyl" refers to an unsubstituted heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—CH₃) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

The phrase "unsubstituted alkylaminoalkyl" refers to an unsubstituted alkyl group as defined above in which a carbon or hydrogen bond is replaced by a bond to a nitrogen atom that is bonded to a hydrogen atom and an unsubstituted alkyl group as defined above. For example, methyl (—CH₃) is an unsubstituted alkyl group. If a hydrogen atom of the methyl group is replaced by a bond to a nitrogen atom that is bonded to a hydrogen atom and an ethyl group, then the resulting compound is —CH₂—N(H)(CH₂CH₃) which is an unsubstituted alkylaminoalkyl group.

The phrase "substituted alkylaminoalkyl" refers to an unsubstituted alkylaminoalkyl group as defined above except where one or more bonds to a carbon or hydrogen atom in one or both of the alkyl groups is replaced by a bond to a non-carbon or non-hydrogen atom as described above with respect to substituted alkyl groups except that the bond to the nitrogen atom in all alkylaminoalkyl groups does not by itself qualify all alkylaminoalkyl groups as being substituted. However, substituted alkylaminoalkyl groups does include groups in which the hydrogen bonded to the nitrogen atom of the group is replaced with a non-carbon and non-hydrogen atom.

The phrase "unsubstituted dialkylaminoalkyl" refers to an unsubstituted alkyl group as defined above in which a carbon bond or hydrogen bond is replaced by a bond to a nitrogen atom which is bonded to two other similar or different unsubstituted alkyl groups as defined above.

The phrase "substituted dialkylaminoalkyl" refers to an unsubstituted dialkylaminoalkyl group as defined above in which one or more bonds to a carbon or hydrogen atom in one or more of the alkyl groups is replaced by a bond to a non-carbon and non-hydrogen atom as described with respect to substituted alkyl groups. The bond to the nitrogen atom in all dialkylaminoalkyl groups does not by itself qualify all dialkylaminoalkyl groups as being substituted.

The phrase "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

The phrase "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

The phrase "unsubstituted arylaminoalkyl" refers to an unsubstituted alkyl group as defined above in which a carbon bond or hydrogen bond is replaced by a bond to a nitrogen atom which is bonded to at least one unsubstituted aryl group as defined above.

The phrase "substituted arylaminoalkyl" refers to an unsubstituted arylaminoalkyl group as defined above except where either the alkyl group of the arylaminoalkyl group is a substituted alkyl group as defined above or the aryl group of the arylaminoalkyl group is a substituted aryl group except that the bonds to the nitrogen atom in all arylaminoalkyl groups does not by itself qualify all arylaminoalkyl groups as being substituted. However, substituted arylaminoalkyl groups does include groups in which the hydrogen bonded to the nitrogen atom of the group is replaced with a non-carbon and non-hydrogen atom.

The phrase "unsubstituted heterocyclylaminoalkyl" refers to an unsubstituted alkyl group as defined above in which a carbon or hydrogen bond is replaced by a bond to a nitrogen atom which is bonded to at least one unsubstituted heterocyclyl group as defined above.

The phrase "substituted heterocyclylaminoalkyl" refers to unsubstituted heterocyclylaminoalkyl groups as defined above in which the heterocyclyl group is a substituted heterocyclyl group as defined above and/or the alkyl group is a substituted alkyl group as defined above. The bonds to the nitrogen atom in all heterocyclylaminoalkyl groups does not by itself qualify all heterocyclylaminoalkyl groups as being substituted. However, substituted heterocyclylaminoalkyl groups do include groups in which the hydrogen bonded to the nitrogen atom of the group is replaced with a non-carbon and non-hydrogen atom.

The phrase "unsubstituted alkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to a hydrogen atom and an unsubstituted alkyl group as defined above.

The phrase "substituted alkylaminoalkoxy" refers to unsubstituted alkylaminoalkoxy groups as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if the hydrogen bonded to the amino group is bonded to a non-carbon and non-hydrogen atom and/or if the alkyl group bonded to the nitrogen of the amine is bonded to a non-carbon and non-hydrogen atom as described above with respect to substituted alkyl groups. The presence of the amine and alkoxy functionality in all alkylaminoalkoxy groups does not by itself qualify all such groups as substituted alkylaminoalkoxy groups.

The phrase "unsubstituted dialkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to two other similar or different unsubstituted alkyl groups as defined above.

The phrase "substituted dialkylaminoalkoxy" refers to an unsubstituted dialkylaminoalkoxy group as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if one or more of the alkyl groups bonded to the nitrogen of the amine is bonded to a non-carbon and non-hydrogen atom as described above with respect to substituted alkyl groups. The presence of the amine and alkoxy functionality in all dialkylaminoalkoxy groups does not by itself qualify all such groups as substituted dialkylaminoalkoxy groups.

The phrase "unsubstituted heterocyclyloxy" refers to a hydroxyl group (—OH) in which the bond to the hydrogen atom is replaced by a bond to a ring atom of an otherwise unsubstituted heterocyclyl group as defined above.

The phrase "substituted heterocyclyloxy" refers to a hydroxyl group (—OH) in which the bond to the hydrogen atom is replaced by a bond to a ring atom of an otherwise substituted heterocyclyl group as defined above.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Compounds having the structure I, tautomers of the compounds, pharmaceutically acceptable salts of the compounds, and pharmaceutically acceptable salts of the tautomers have been found to inhibit VEGF-RTK. Structure I has the following formula.

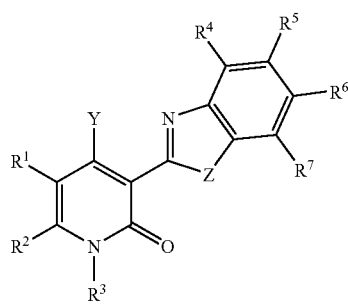

I

In compounds of structure I, Y is selected from —OH, —OR$^8$ groups, —SH, —SR$^9$ groups, —NR$^{10}$R$^{11}$ groups, —CN, —C(=O)—R$^{12}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. In more preferred compounds having the structure I, Y is —OH, an —OR$^8$ group, or a —NR$^{10}$R$^{11}$ group. More preferably, Y is a —NR$^{10}$R$^{11}$ group, where, one of R$^{10}$ or R$^{11}$ is H or where R$^{10}$ and R$^{11}$ are both H.

In yet other compounds having the structure I, Y is selected from —N(CH$_3$)$_2$, —NH(CH$_3$), —NH(CH$_2$CH$_3$), —N(CH$_2$CH$_3$)$_2$, —NH(aryl) groups, —N(aryl)$_2$ groups, —NHNH$_2$, —NHN(CH$_3$)$_2$, —N(CH$_3$)NH(CH$_3$), —NH(CH$_2$)$_m$NH$_2$ groups, —NH(CH$_2$)$_m$NH(alkyl) groups, —NH(CH$_2$)$_m$N(alkyl)$_2$ groups, —N(alkyl)(CH$_2$)$_m$NH$_2$ groups, —N(alkyl)(CH$_2$)$_m$NH(alkyl) groups, —N(alkyl)(CH$_2$)$_m$N(alkyl)$_2$ groups, —NH(CH$_2$)$_n$(heterocyclyl) groups, —N(alkyl)[(CH$_2$)$_n$(heterocyclyl)] groups, —NH(CH$_2$)$_m$OH groups, —NH(CH$_2$)$_m$OCH$_3$ groups, —NHCH$_2$CH(NH$_2$)CH (CH$_3$)$_2$, —NH(2-aminocyclohexyl), —NH(cyclohexyl), —NHOCH$_3$, —NH(N-morpholinyl), —NH(quinuclidyl), especially —NH(quinuclid-3-yl), and groups where R$^{10}$ and R$^{11}$ join to form a substituted or unsubstituted saturated 5 or 6 membered N-containing ring, where m is 2, 3, or 4 and n is 0, 1, 2, or 3. Still more preferred compounds of this type are compounds in which Y is —NH(5-benzimidazolyl), —NH(CH$_2$)$_2$N(CH$_3$)$_2$, —NH(CH$_2$)$_2$OH, —NH(CH$_2$)(4-imidazolyl), —NH(CH$_2$)(3-imidazolyl), —NH(CH$_2$)(4-pyridyl), —NH(CH$_2$)(2-pyridyl), —NH(CH$_2$)(3-pyridyl), —NH(CH$_2$)(2-tetrahydrofuranyl), —NH(CH$_2$)(4-piperidinyl), —NH(CH$_2$)(3-piperidinyl), —NH(CH$_2$)$_2$[2-(N-methyl-pyrrolidinyl)], —NH(CH$_2$)$_2$(2-pyrrolidinyl), —NH (CH$_2$)[2-(N-methylpyrrolidinyl)], —NH(CH$_2$)(2-pyrrolidinyl), —NH(3-piperidinyl), or —NH(3-pyrrolidinyl).

Z is O, S, or a NR$^{13}$ group in compounds of structure I. Preferably, Z is a NR$^{13}$ group and, even more preferably, R$^{13}$ is H.

In compounds of structure I, R$^1$ and R$^2$ join to form a 5 to 7 membered substituted or unsubstituted ring including at least one O, N, or S atom. In some embodiments, R$^1$ and R$^2$ join together to form a 5 or 6 membered substituted or unsubstituted ring including one N atom, one O atom, or one S atom. In other embodiments R$^1$ and R$^2$ join together to form a 5 or 6 membered ring including two heteroatoms selected from O, N, or S. An example of an embodiment in which R$^1$ and R$^2$ join together to form a 5 membered ring having two N atoms are compounds having the formula IA described below. Another example of an embodiment in which R$^1$ and R$^2$ join together to form a 5 membered ring having two N atoms are compounds having the formula IB described below. An example of an embodiment in which R$^1$ and R$^2$ form a 5 membered ring having one S atom are compounds having the formula IC described below. Examples of embodiments in which R$^1$ and R$^2$ join together to form a 6 membered ring containing one or more N atom are compounds having the formula II below.

R$^3$ and R$^{13}$ may be the same or different in compounds of structure I and may be H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted and unsubstituted heterocyclylamino groups, substituted and unsubstituted diheterocyclylamino groups, substituted and unsubstituted (alkyl)(heterocyclyl)amino groups, substituted and unsubstituted (aryl)(heterocyclyl)amino groups, substituted and unsubstituted heterocylyloxy groups, substituted or unsubstituted alkyl groups, substituted or unsubstituted aryl groups, —C(=O)H, —C(=O)-alkyl groups, or —C(=O)-aryl groups. In more preferred compounds of structure I, R$^3$ is H.

R⁴, R⁵, R⁶, and R⁷ may be the same or different in compounds of structure I and are independently selected from H, Cl, Br, F, I, —NO₂, —CN, —OH, —OR¹⁴ groups, —NR¹⁵R¹⁶ groups, —C(=O)R¹⁷ groups, —SH, —SR¹⁸ groups, —S(=O)R¹⁹ groups, S(=O)₂R²⁰ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. R⁴ and R⁵ may join to form a 5 to 7 membered substituted or unsubstituted carbocyclic or heterocyclic ring. Similarly, R⁵ and R⁶ may join to form a 5 to 7 membered substituted or unsubstituted carbocyclic or heterocyclic ring. Finally, R⁶ and R⁷ may also join to form a 5 to 7 membered substituted or unsubstituted carbocyclic or heterocyclic ring.

In one group of preferred compounds of structure I, R⁴, R⁵, R⁶, and R⁷ are all H. In other more preferred compounds of structure I, R⁵, R⁶ or both R⁵ and R⁶ are alkyl groups having from one to four carbon atoms. In still other preferred compounds having the formula of structure I, R⁵ or R⁶ is an —OR¹⁴ group and R¹⁴ is an alkyl, aryl, heterocyclyl, or heterocyclylalkyl group. In still further preferred compounds of structure I, R⁵ or R⁶ is a —OCH₂(CH₂)_q(heterocyclyl) group where q is 0, 1, 2, 3, or 4. More preferably the heterocyclyl group of the —OCH₂(CH₂)_q(heterocyclyl) group is a heterocycle selected from substituted or unsubstituted morpholine, substituted or unsubstituted piperazine, substituted or unsubstituted piperidine, substituted or unsubstituted pyrrolidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted furan, substituted or unsubstituted thiophene, substituted or unsubstituted tetrahydrofuran, substituted or unsubstituted tetrahydrothiophene, substituted or unsubstituted benzimidazole, substituted or unsubstituted benzoxazole, or substituted or unsubstituted benzothiazole.

In still other preferred compounds having the structure I, at least one of R⁴, R⁵, R⁶, or R⁷ is a substituted or unsubstituted heterocyclyl group, more specifically a substituted or unsubstituted heterocyclyl group comprising at least one O or N atom, and more particularly a substituted or unsubstituted heterocyclyl group selected from morpholine, piperazine, piperidine, 1,2,3-triazole, 1,2,4-triazole, tetrazole, pyrrolidine, pyrazole, pyrrole, thiomorpholine, homopiperazine, benzimidazole, oxazolidin-2-one, pyrrolidin-2-one, imidazole, isoxazole, oxazole, isothiazole, thiazole, thiophene, furan, pyran, tetrahydrothiophene, tetrahydrofuran, tetrahydropyran, and pyridine.

In groups including heterocyclyl groups, the heterocycle may be attached in various ways. For example in the —OCH₂(CH₂)_q(heterocyclyl) group, the heterocyclyl group may be bonded to a methylene carbon of the —OCH₂(CH₂)_q group of the —OCH₂(CH₂)_q(heterocyclyl) group through various ring members. By way of non-limiting example, where q is 1 and the heterocyclyl group is tetrahydrofuran, the group could be represented by the formula —OCH₂CH₂-(tetrahydrofuranyl) which corresponds to the following two structures:

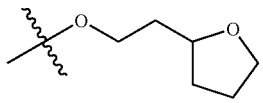
IV

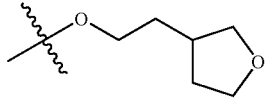
V where structure IV represents the group that can be referred to as the —OCH₂CH₂(2-tetrahydrofuranyl) group and structure V represents the group that can be referred to as the —OCH₂CH₂(3-tetrahydrofuranyl) group. When the heterocyclyl group is a N-containing heterocycle, such as, but not limited to piperidine, piperazine, morpholine, or pyrrolidine, the heterocycle can be bonded to the methylene carbon through a ring carbon atom or through a nitrogen atom in the ring of the N-containing heterocycle. Both of these are preferred. Where the heterocyclyl group is a piperidine and q is 2 for a —OCH₂(CH₂)_q(heterocyclyl) group, the following structures are possible and preferred:

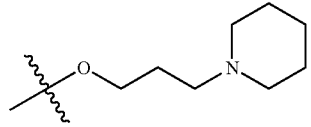
VI

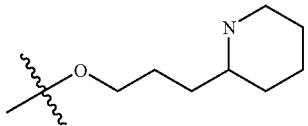
VII

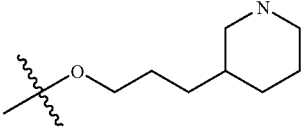
VIII

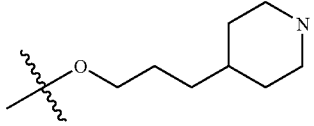
IX

Structure VI is an example of a —O(CH₂)₃(N-piperidinyl) or —O(CH₂)₃(1-piperidinyl) group. Structure VII is an example of a —O(CH₂)₃(2-piperidinyl) group. Structure VIII is an example of a —O(CH$_2$)$_3$(3-piperidinyl) group. Structure IX is an example of a —O(CH$_2$)$_3$(4-piperidinyl) group. Where the heterocyclyl group is a piperazine and q is 1 for an —OCH$_2$(CH$_2$)$_q$(heterocyclyl) group, the following structures are possible and preferred:

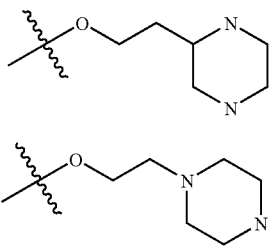

Structure X is an example of a —O(CH$_2$)$_2$(2-piperazinyl) group, and structure XI is an example of a —O(CH$_2$)$_2$(1-piperazinyl) or —O(CH$_2$)$_2$(N-piperazinyl) group. Where the heterocyclyl group is a morpholine and q is 1 for an —OCH$_2$(CH$_2$)$_q$-heterocyclyl) group, the following structures are possible and preferred:

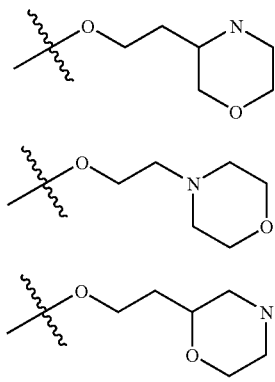

Structure XII is an example of a —O(CH$_2$)$_2$(3-morpholinyl) group, structure XIII is an example of a —O(CH$_2$)$_2$(4-morpholinyl) or —O(CH$_2$)$_2$(N-morpholinyl) group, and structure XIV is an example of a —O(CH$_2$)$_2$(2-morpholinyl) group. It will be observed that where the group is a pyrrolidine, and q is 1, the structures available include —O(CH$_2$)$_2$(1-pyrrolidinyl) or —O(CH$_2$)$_2$(N-pyrrolidinyl), —O(CH$_2$)$_2$(2-pyrrolidinyl), and —O(CH$_2$)$_2$(3-pyrrolidinyl).

In compounds of structure I, R$^8$ may be a substituted or unsubstituted alkyl group, a substituted or unsubstituted aryl group, a substituted or unsubstituted heterocyclyl group, a substituted or unsubstituted heterocyclylalkyl group, —C(=O)H, a —C(=O)-alkyl group, a —C(=O)-aryl group, a —C(=O)O-alkyl group, a —C(=O)O-aryl group, —C(=O)NH$_2$, a —C(=O)NH(alkyl) group, a —C(=O)NH(aryl) group, a —C(=O)N(alkyl)$_2$ group, a —C(=O)N(aryl)$_2$ group, a —C(=O)N(alkyl)(aryl) group, —NH$_2$, a —NH(alkyl) group, a —NH(aryl) group, a —N(alkyl)$_2$ group, a —N(alkyl)(aryl) group, a —N(aryl)$_2$ group, a —C(=O)NH(heterocyclyl) group, a —C(=O)N(heterocyclyl)$_2$ group, a —C(=O)N(alkyl)(heterocyclyl) group, or a —C(=O)N(aryl)(heterocyclyl) group.

R$^9$ and R$^{18}$ may be the same or different in compounds of structure I and are independently selected from substituted or unsubstituted alkyl groups, or substituted or unsubstituted aryl groups.

In compounds of structure I, R$^{10}$ is selected from H, substituted or unsubstituted alkyl groups, substituted or unsubstituted aryl groups, or substituted or unsubstituted heterocyclyl groups, and R$^{11}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. R$^{10}$ and R$^{11}$ may join together to form a 5 to 7 membered saturated or unsaturated, substituted or unsubstituted N-containing ring.

In compounds of structure I, R$^{12}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups.

In structure I, R$^{14}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)-heterocyclyl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)NH-heterocyclyl groups, —C(=O)N-(heterocyclyl)$_2$ groups, —C(=O)N(alkyl)(heterocyclyl) groups, —C(=O)N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups.

In compounds of structure I, R¹⁵ is selected from H, substituted or unsubstituted alkyl groups, substituted or unsubstituted aryl groups, or substituted or unsubstituted heterocyclyl groups. R¹⁶ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH₂, —C(=O)NH(alkyl) groups, —C(=O)NH(aryl) groups, —C(=O)N(alkyl)₂ groups, —C(=O)N(aryl)₂ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)₂ groups, —C(=O)—N(alkyl)(heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. R¹⁵ and R¹⁶ may join together to form a 5 to 7 membered saturated or unsaturated, substituted or unsubstituted N-containing ring.

R¹⁷, R¹⁹, and R²⁰ may be the same or different and are independently selected from H, —NH₂, —NH(alkyl) groups, —NH(aryl) groups, —N(alkyl)₂ groups, —N(aryl)₂ groups, —N(alkyl)(aryl) groups, —NH(heterocyclyl) groups, —N(heterocyclyl)(alkyl) groups, —N(heterocyclyl)(aryl) groups, —N(heterocyclyl)₂ groups, substituted and unsubstituted alkyl groups, substituted and unsubstituted aryl groups, —OH, substituted and unsubstituted alkoxy groups, substituted and unsubstituted heterocyclyl groups, substituted and unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups.

In some preferred compounds of structure I, R¹⁷ is selected from unsubstituted alkyl groups, substituted or unsubstituted aryl groups, —NH₂, —NH(alkyl) groups, —N(alkyl)₂ groups, —NH(aryl) groups, —N(aryl)₂ groups, —N(alkyl)(aryl) groups, —NH(heterocyclyl) groups, —N(heterocyclyl)(alkyl) groups, —N(heterocyclyl)(aryl) groups, —N(heterocyclyl)₂ groups, or N-containing heterocycles, and the N-containing heterocycles are bonded to the carbonyl carbon of the —C(=O)—R¹⁷ group through either a nitrogen atom or a carbon atom in the rings of the N-containing heterocycles. In still more preferred compounds in which R¹⁷ is a N-containing heterocycle, the N-containing heterocycle of the R¹⁷ group is selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

In other preferred compounds having structure I, R¹⁴ or R¹⁶ is selected from substituted or unsubstituted aminoalkyl groups, substituted or unsubstituted alkylaminoalkyl groups, substituted or unsubstituted arylaminoalkyl groups, substituted or unsubstituted dialkylaminoalkyl groups, substituted or unsubstituted diarylaminoalkyl groups, alkylarylaminoalkyl groups, or substituted or unsubstituted heterocyclalkyl groups, including: —CH₂(CH₂)ₚNH₂ groups, —CH₂(CH₂)ₚNH(alkyl) groups, —CH₂(CH₂)ₚNH(aryl) groups, —CH₂(CH₂)ₚN(alkyl)₂ groups, —CH₂(CH₂)ₚN(aryl)₂ groups, —CH₂(CH₂)ₚN(alkyl)(aryl) groups, or —CH₂(CH₂)ₚ(heterocyclyl) groups, where p is an integer ranging from 0 to 4 and the heterocyclyl group of the —CH₂(CH₂)ₚ(heterocyclyl) group is a N-containing heterocycle selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Other compounds having the structure I are provided that also have the structure IA. These are compounds in which R¹ and R² of structure I join together to form a 5 membered ring having having two N atoms.

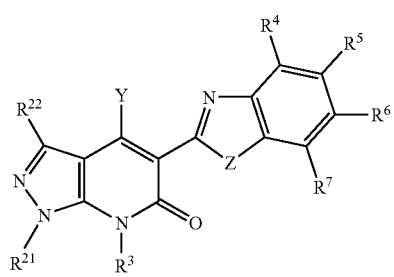

IA

In compounds of structure IA, R²¹ is selected from H or substituted or unsubstituted alkyl groups; R²² may be the same or different from R⁴, R⁵, R⁶, R⁷ and is independently selected from H, Cl, Br, F, I, —NO₂, —CN, —OH, —OR¹⁴ groups, —NR¹⁵R¹⁶ groups, —C(=O)R¹⁷ groups, —SH, —SR¹⁸ groups, —S(=O)R¹⁹ groups, S(=O)₂R²⁰ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; and $R^3$ through $R^{21}$ have the values described above with respect to compounds of structure I.

Other compounds of structure IA are those in which Z is an $NR^{13}$ and more preferably where $R^{13}$ is H. Other compounds of structure IA are provided in which $R^3$ is H.

Still other compounds of structure IA are those in which Y is an —$NR^{10}R^{11}$ group. In still other compounds of structure IA, Y is an —$NR^{10}R^{11}$ group and $R^{10}$ and $R^{11}$ are hydrogen atoms.

Still other compounds having the structure I are provided that have the structure IB. Like compounds of structure IA, these are compounds in which $R^1$ and $R^2$ of structure I join together to form a 5 membered ring having having two N atoms.

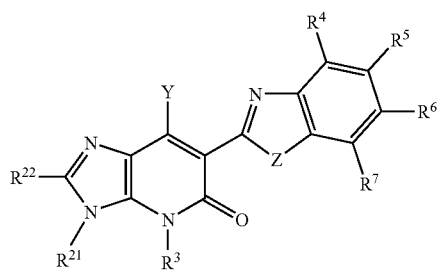

IB

In compounds of structure IB, $R^{21}$ is selected from H or substituted or unsubstituted alkyl groups; $R^{22}$ may be the same or different from $R^4$, $R^5$, $R^6$, $R^7$ and is independently selected from H, Cl, Br, F, I, —$NO_2$, —CN, —OH, —$OR^{14}$ groups, —$NR^5R^{16}$ groups, —C(=O)$R^{17}$ groups, —SH, —$SR^{18}$ groups, —S(=O)$R^{19}$ groups, S(=O)$_2R^{20}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; and $R^3$ through $R^{21}$ have the values described above with respect to compounds of structure I.

Other compounds of structure IB include those in which Z is an $NR^{13}$ and more preferably those where $R^{13}$ is H.

Other compounds of structure IB are those in which $R^3$ is H.

Still other compounds of structure IB are those in which Y is an —$NR^{10}R^{11}$ group. In still other compounds of structure IB, Y is an —$NR^{10}R^{11}$ group and $R^{10}$ and $R^{11}$ are hydrogen atoms.

Still other compounds having the structure I are provided that have the structure IC. These are compounds in which $R^1$ and $R^2$ of structure I join together to form a 5 membered ring having having one S atom.

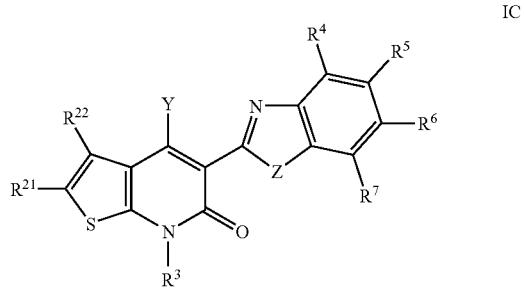

IC

In compounds of structure IC, $R^{21}$ and $R^{22}$ may be the same or different from $R^4$, $R^5$, $R^6$, $R^7$ and each other and are independently selected from H, Cl, Br, F, I, —$NO_2$, —CN, —OH, —$OR^{14}$ groups, —$NR^{15}R^{16}$ groups, —C(=O)$R^{17}$ groups, —SH, —$SR^{18}$ groups, —S(=O)$R^{19}$ groups, S(=O)$_2$ $R^{20}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; and $R^3$ through $R^{20}$ have the values described above with respect to compounds of structure I.

Other compounds of structure IC are those in which Z is an $NR^{13}$ and more preferably those where $R^{13}$ is H. Other compounds of structure IC are those in which $R^3$ is H.

Still other compounds of structure IC are those in which Y is an —$NR^{10}R^{11}$ group. In still other compounds of structure IC, Y is an —$NR^{10}R^{11}$ group and $R^{10}$ and $R^{11}$ are hydrogen atoms.

Particularly preferred inhibitors of VEGF-RTK are compounds having the structure II, tautomers of the compounds, pharmaceutically acceptable salts of the compounds, and pharmaceutically acceptable salts of the tautomers. These are compounds having a ring system similar to that of Structure I where $R^1$ and $R^2$, as defined above with respect to Structure I, join together to form a 6 membered ring that includes at least one N atom. Structure II has the following formula:

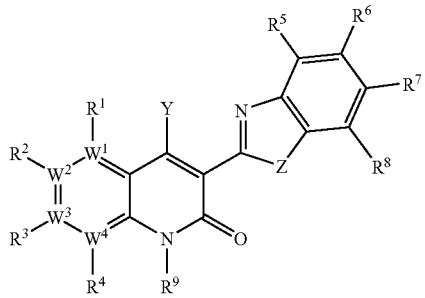

II

In compounds of structure II, $W^1$, $W^2$, $W^3$, and $W^4$ are selected from C or N, and at least one of $W^1$, $W^2$, $W^3$, or $W^4$ is N. In some preferred compounds of structure II, $W^1$ is N and $R^1$ is absent or H. In other preferred compounds of structure II, $W^2$ is N and $R^2$ is absent or H. In still other preferred compounds of structure II, $W^3$ is N and $R^3$ is absent or H. In yet other preferred compounds of structure II, $W^4$ is N and $R^4$ is absent or H. In some preferred compounds of structure II, one of $W^1$, $W^2$, $W^3$, and $W^4$ is N. In other preferred compounds of structure II, two of $W^1$, $W^2$, $W^3$, and $W^4$ are N. In yet other preferred embodiments, $W^1$, $W^2$, and $W^3$ are all C and $W^4$ is N; $W^1$, $W^2$, and $W^4$ are all C and $W^3$ is N; $W^1$, $W^3$, and $W^4$ are all C and $W^2$ is N; or $W^2$, $W^3$, and $W^4$ are all C and $W^1$ is N.

In compounds having structure II, Y is selected from —OH, —OR$^{10}$ groups, —SH, —SR$^{11}$ groups, —NR$^{12}$R$^{13}$ groups, —CN, —C(=O)—R$^{14}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups.

In preferred compounds of structure II, Y is selected from —OH, —OR$^{10}$ groups, or —NR$^{12}$R$^{13}$ groups, or more preferably —NR$^{12}$R$^{13}$ groups, or still more preferably —NR$^{12}$R$^{13}$ groups where one or both of $R^{12}$ and $R^{13}$ are H. In other preferred compounds having the structure II, Y is selected from —N(CH$_3$)$_2$, —NH(CH$_3$), —NH(CH$_2$CH$_3$), —N(CH$_2$CH$_3$)$_2$, —NH(aryl) groups, —N(aryl)$_2$ groups, —NHNH$_2$, —NHN(CH$_3$)$_2$, —N(CH$_3$)NH(CH$_3$), —NH(CH$_2$)$_m$NH$_2$ groups, —NH(CH$_2$)$_m$NH(alkyl) groups, —NH(CH$_2$)$_m$N(alkyl)$_2$ groups, —N(alkyl)(CH$_2$)$_m$NH$_2$ groups, —N(alkyl)(CH$_2$)$_m$NH(alkyl) groups, —N(alkyl)(CH$_2$)$_m$N(alkyl)$_2$ groups, —NH(CH$_2$)$_n$(heterocyclyl) groups, —N(alkyl)[(CH$_2$)$_n$(heterocyclyl)] groups, —NH(CH$_2$)$_m$OH groups, —NH(CH$_2$)$_m$OCH$_3$ groups, —NHCH$_2$CH(NH$_2$)CH(CH$_3$)$_2$, —NH(2-aminocyclohexyl), —NH(cyclohexyl), —NHOCH$_3$, —NH(N-morpholinyl), —NH(quinuclidyl), especially —NH(quinuclid-3-yl), and groups where $R^{12}$ and $R^{13}$ join to form a substituted or unsubstituted saturated 5 or 6 membered N-containing ring, where m is 2, 3, or 4 and n is 0, 1, 2, or 3. Still more preferred compounds of this type are those in which Y is selected from —NH(5-benzimidazolyl), —NH(CH$_2$)$_2$N(CH$_3$)$_2$, —NH(CH$_2$)$_2$OH, —NH(CH$_2$)(4-imidazolyl), —NH(CH$_2$)(3-imidazolyl), —NH(CH$_2$)(4-pyridyl), —NH(CH$_2$)(2-pyridyl), —NH(CH$_2$)(3-pyridyl), —NH(CH$_2$)(2-tetrahydrofuranyl), —NH(CH$_2$)(4-piperidinyl), —NH(CH$_2$)(3-piperidinyl), —NH(CH$_2$)$_2$[2-(N-methyl-pyrrolidinyl)], —NH(CH$_2$)$_2$(2-pyrrolidinyl), —NH(CH$_2$)[2-(N-methylpyrrolidinyl)], —NH(CH$_2$)(2-pyrrolidinyl), —NH(3-piperidinyl), or —NH(3-pyrrolidinyl).

In compound of structure II, Z is O, S, and NR$^{15}$ groups. In preferred compounds of structure II, Z is an NR$^{15}$ group or more preferably is an NR$^{15}$ group where $R^{15}$ is H.

In compounds of structure II, $R^1$, $R^2$, $R^3$, $R^4$, $R^5$, $R^6$, $R^7$, and $R^8$ may be the same or different and are independently selected from H, Cl, Br, F, I, —NO$_2$, —CN, —OH, —OR$^{16}$ groups, —NR$^{17}$R$^{18}$ groups, —C(=O)R$^{19}$ groups, —SH, —SR$^{20}$ groups, —S(=O)R$^{21}$ groups, S(=O)$_2$R$^{22}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups, and $R^1$ is absent or H if $W^1$ is N, $R^2$ is absent or H if $W^2$ is N, $R^3$ is absent or H if $W^3$ is N, and $R^4$ is absent or H if $W^4$ is N.

Some preferred compounds have the structure II where at least one of $R^1$, $R^2$, $R^3$, $R^4$, $R^5$, $R^6$, $R^7$, or $R^8$ is a substituted or unsubstituted heterocyclyl group, and in more preferred embodiments, a substituted or unsubstituted heterocyclyl group selected from morpholine, piperazine, piperidine, 1,2,3-triazole, 1,2,4-triazole, tetrazole, pyrrolidine, pyrazole, pyrrole, thiomorpholine, homopiperazine, benzimidazole, oxazolidin-2-one, pyrrolidin-2-one, imidazole, isothiazole, thiazole, thiophene, furan, pyran, tetrahydrothiophene, tetrahydrofuran, tetrahydropyran, and pyridine.

Still other preferred compounds having structure II are those in which $R^1$, $R^2$, and $R^3$ are H, and $W^4$ is N. Still other compounds having the formula of structure II are provided in which $R^2$, $R^3$, and $R^4$ are H, and $W^1$ is N. Still other compounds having the formula of structure II are provided in which $R^1$, $R^3$, and $R^4$ are H, and $W^2$ is N. Still other compounds having the formula of structure II are provided in which $R^1$, $R^2$, and $R^4$ are H, and $W^3$ is N.

In other preferred compounds, $R^1$ or $R^2$ is selected from F, Cl, substituted or unsubstituted alkoxy groups, substituted or unsubstituted heterocyclyloxy groups, substituted or unsubstituted heterocyclylalkoxy groups, substituted or unsubstituted heterocyclyl groups, substituted or unsubstituted alkyl-, heterocycyl-, or aryl-aminoalkyl groups, substituted or unsubstituted dialkyl- or diaryl-aminoalkyl groups, substituted or unsubstituted alkylarylaminoalkyl groups, substituted or unsubstituted alkyl- and aryl-aminoalkoxy groups, substituted or unsubstituted dialkyl- and diaryl-aminoalkoxy groups, or substituted or unsubstituted alkylarylaminoalkoxy groups. Particular examples include: —C(=O)N(alkyl)$_2$ groups, —OCH$_2$CH$_2$(N-morpholinyl), N-morpholinyl, —OCH$_2$CH$_2$N(alkyl)$_2$ groups, —OCH$_2$CH$_2$NH(alkyl) groups, —OCH$_2$CH$_2$NH$_2$, —OCH$_2$CH$_2$NH(aryl) groups, —OCH$_2$CH$_2$N(aryl)$_2$ groups, alkoxy groups, —OCH$_2$CH$_2$N(alkyl)(aryl) groups, —O(4-piperidinyl), —O[4-(1-alkyl)piperidinyl] groups, —OCH$_2$(2-pyridyl), —O(3-pyrrolidinyl), or —O[3-(1-alkyl)pyrrolidinyl] groups.

Still other preferred compounds include those in which $R^2$ is selected from F, Cl, —NO$_2$, substituted or unsubstituted alkoxy groups, substituted or unsubstituted heterocyclylalkoxy groups, substituted or unsubstituted heterocyclyl groups, substituted or unsubstituted alkyl-, heterocycyl-, or aryl-aminoalkyl groups, substituted or unsubstituted dialkyl- and diaryl-aminoalkyl groups, substituted or unsubstituted alkylarylaminoalkyl groups, substituted or unsubstituted alkyl- and aryl-aminoalkoxy groups, substituted or unsubstituted dialkyl- and diaryl-aminoalkoxy groups, substituted or unsubstituted alkylarylaminoalkoxy groups. Particular examples include: —OCH$_3$, N-morpholinyl, —N-cis-dialkylmorpholinyl, —N-(4-alkyl)piperazinyl, or —OCH$_2$(2-pyridyl).

In yet preferred compounds having structure II, $R^5$, $R^6$, $R^7$, and $R^8$ are hydrogen. In still other more preferred compounds of structure II, $R^6$, $R^7$ or both $R^6$ and $R^7$ are alkyl groups having from one to four carbon atoms. In yet other preferred compounds of structure II, $R^6$ or $R^7$ is an —OR$^{16}$ group and $R^{16}$ is an alkyl, aryl, heterocyclyl, or heterocyclylalkyl group. In still further preferred compounds of structure II, $R^6$ or $R^7$ is a —OCH$_2$(CH$_2$)$_q$(heterocyclyl) group and q is 0, 1, 2, 3, or 4. In more preferred compounds in which $R^6$ or $R^7$ is a —OCH$_2$(CH$_2$)$_q$-(heterocyclyl) group, the heterocyclyl group of the —OCH$_2$(CH$_2$)$_n$(heterocyclyl) group is a heterocycle selected from substituted or unsubstituted morpholine, substituted or unsubstituted piperazine, substituted or unsubstituted piperidine, substituted or unsubstituted pyrrolidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or substituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted furan, substituted or unsubstituted thiophene, substituted or unsubstituted tetrahydrofuran, substituted or unsubstituted tetrahydrothiophene, substituted or unsubstituted benzimidazole, substituted or unsubstituted benzoxazole, or substituted or unsubstituted benzothiazole.

In compounds of structure II, $R^9$ and $R^{15}$ may be the same or different and are selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups. In preferred compounds of structure II, $R^9$ is hydrogen.

In compounds of structure II, $R^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)—N(alkyl)(heterocyclyl) groups, or —C(=O)N(aryl)(heterocyclyl) groups.

$R^{11}$ and $R^{20}$ may be the same or different in compounds of structure II and are independently selected from substituted or unsubstituted alkyl groups, or substituted or unsubstituted aryl groups.

In compounds of structure II, $R^{12}$ is selected from H, substituted or unsubstituted alkyl groups, substituted or unsubstituted aryl groups, or substituted or unsubstituted heterocyclyl groups whereas $R^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. $R^{12}$ and $R^{13}$ may join together to form a 5 to 7 membered saturated or unsaturated, substituted or unsubstituted N-containing ring.

In compounds of structure II, $R^{14}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups.

In compounds of structure II, $R^{16}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)-heterocyclyl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)NH-heterocyclyl groups, —C(=O)N-(heterocyclyl)$_2$ groups, —C(=O)N(alkyl)(heterocyclyl) groups, —C(=O)N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups.

In compounds of structure II, $R^{17}$ is selected from H, substituted or unsubstituted alkyl groups, substituted or unsubstituted aryl groups, or substituted or unsubstituted heterocyclyl groups whereas $R^{18}$ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (aryl)(alkyl)aminoalkyl groups, substituted or unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. $R^{17}$ and $R^{18}$ may join together to form a 5 to 7 membered saturated or unsaturated, substituted or unsubstituted N-containing ring.

Finally, in compounds of structure II, $R^{19}$, $R^{21}$, and $R^{22}$ may be the same or different and are independently selected from H, —$NH_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups.

Preferred compounds having the structure II include those in which $R^{19}$ is selected from substituted or unsubstituted alkyl groups, substituted or unsubstituted aryl groups, —$NH_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, or N-containing heterocycles, and the N-containing heterocycles are bonded to the carbonyl carbon of the —C(=O)—$R^{19}$ group through either a nitrogen atom or a carbon atom in the rings of the N-containing heterocycles. In still more preferred compounds in which $R^{19}$ is a N-containing heterocycle, the N-containing heterocycle of the $R^{19}$ group is selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Other preferred compounds having structure II are provided in which $R^{16}$ or $R^{18}$ is selected from substituted or unsubstituted aminoalkyl groups, substituted or unsubstituted alkylaminoalkyl groups, substituted or unsubstituted arylaminoalkyl groups, substituted or unsubstituted dialkylaminoalkyl groups, substituted or unsubstituted diarylaminoalkyl groups, alkylarylaminoalkyl groups, or substituted or unsubstituted heterocycylalkyl groups, including: —$CH_2$($CH_2$)$_p$$NH_2$ groups, —$CH_2$($CH_2$)$_p$NH(alkyl) groups, —$CH_2$($CH_2$)$_p$NH(aryl) groups, —$CH_2$($CH_2$)$_p$N(alkyl)$_2$ groups, —$CH_2$($CH_2$)$_p$N(aryl)$_2$ groups, —$CH_2$($CH_2$)$_p$N(alkyl)(aryl) groups, or —$CH_2$($CH_2$)$_p$(heterocyclyl) groups, where p is an integer ranging from 0 to 4 and the heterocyclyl group of the —$CH_2$($CH_2$)$_p$(heterocyclyl) group is a N-containing heterocycle selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Other particularly preferred inhibitors of VEGF-RTK are compounds having the structure III, tautomers of the compounds, pharmaceutically acceptable salts of the compounds, and pharmaceutically acceptable salts of the tautomers. Structure III has the following formula:

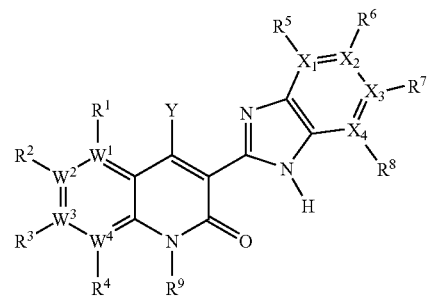

III

In compounds of structure III, $W^1$, $W^2$, $W^3$, and $W^4$ are selected from C or N, and at least one of $W^1$, $W^2$, $W^3$, or $W^4$ is N. In some preferred compounds of structure III, $W^1$ is N and $R^1$ is absent or H. In other preferred compounds of structure III, $W^2$ is N and $R^2$ is absent or H. In still other preferred compounds of structure III, $W^3$ is N and $R^3$ is absent or H. In yet other preferred compounds of structure III, $W^4$ is N and $R^4$ is absent or H. In other preferred compounds of structure III, one of $W^1$, $W^2$, $W^3$, and $W^4$ is N whereas in other compounds of structure III, two of $W^1$, $W^2$, $W^3$, and $W^4$ are N. In yet other preferred embodiments, $W^1$, $W^2$, and $W^3$ are all C and $W^4$ is N; $W^1$, $W^2$, and $W^4$ are all C and $W^3$ is N; $W^1$, $W^3$, and $W^4$ are all C and $W^2$ is N; or $W^2$, $W^3$, and $W^4$ are all C and $W^1$ is N.

In compounds of structure III, $X^1$, $X^2$, $X^3$, and $X^4$ are selected from C or N, and at least one of $X^1$, $X^2$, $X^3$, or $X^4$ is N. In some preferred compounds of structure III, $X^1$ is N and $R^5$ is absent or H. In other preferred compounds of structure III, $X^2$ is N and $R^6$ is absent or H. In still other preferred compounds of structure III, $X^3$ is N and $R^7$ is absent or H. In yet other preferred compounds of structure III, $X^4$ is N and $R^8$ is absent or H. In other preferred compounds of structure III, one of $X^1$, $X^2$, $X^3$, and $X^4$ is N whereas in other compounds of structure III, two of $X^1$, $X^2$, $X^3$, and $X^4$ are N.

In compounds having structure III, Y is selected from H, —OH, —OR$^{10}$ groups, —SH, —SR$^{11}$ groups, —NR$^{12}$R$^{13}$ groups, —CN, —C(=O)—R$^{14}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups.

In preferred compounds of structure III, Y is selected from H, —OH, —OR$^{10}$ groups, or —NR$^{12}$R$^{13}$ groups. More preferably, Y is a —NR$^{12}$R$^{13}$ group. Still more preferably, Y is a —NR$^{12}$R$^{13}$ group and both R$^{12}$ and R$^{13}$ are hydrogen. In other preferred compounds having the structure III, Y is selected from —N(CH$_3$)$_2$, —NH(CH$_3$), —NH(CH$_2$CH$_3$), —N(CH$_2$CH$_3$)$_2$, —NH(aryl) groups, —N(aryl)$_2$ groups, —N(aryl)$_2$ groups, —NHNH$_2$, —NHN(CH$_3$)$_2$, —N(CH$_3$)NH(CH$_3$), —NH(CH$_2$)$_m$NH$_2$ groups, —NH(CH$_2$)$_m$NH(alkyl) groups —NH(CH$_2$)$_m$N(alkyl)$_2$ groups, —N(alkyl)(CH$_2$)$_m$NH$_2$ groups, —N(alkyl)(CH$_2$)$_m$NH(alkyl) groups, —N(alkyl)(CH$_2$)$_m$N(alkyl)$_2$ groups, —NH(CH$_2$)$_n$(heterocyclyl) groups, —N(alkyl)[(CH$_2$)$_n$(heterocyclyl)] groups, —NH(CH$_2$)$_m$OH groups, —NH(CH$_2$)$_m$OCH$_3$ groups, —NHCH$_2$CH(NH$_2$)CH(CH$_3$)$_2$, —NH(2-aminocyclohexyl), —NH(cyclohexyl), —NHOCH$_3$, —NH(N-morpholinyl), —NH(quinuclidyl), especially —NH(quinuclid-3-yl), and groups where R$^{12}$ and R$^{13}$ join to form a substituted or unsubstituted saturated 5 or 6 membered N-containing ring, where m is 2, 3, or 4 and n is 0, 1, 2, or 3. Still more preferred compounds of this type are those in which Y is selected from —NH(5-benzimidazolyl), —NH(CH$_2$)$_2$N(CH$_3$)$_2$, —NH(CH$_2$)$_2$OH, —NH(CH$_2$)(4-imidazolyl), —NH(CH$_2$)(3-imidazolyl), —NH(CH$_2$)(4-pyridyl), —NH(CH$_2$)(2-pyridyl), —NH(CH$_2$)(3-pyridyl), —NH(CH$_2$)(2-tetrahydrofuranyl), —NH(CH$_2$)(4-piperidinyl), —NH(CH$_2$)(3-piperidinyl), —NH(CH$_2$)$_2$[2-(N-methyl-pyrrolidinyl)], —NH(CH$_2$)$_2$(2-pyrrolidinyl), —NH(CH$_2$)[2-(N-methylpyrrolidinyl)], —NH(CH$_2$)(2-pyrrolidinyl), —NH(3-piperidinyl), or —NH(3-pyrrolidinyl).

In compounds of structure III, $R^1$, $R^2$, $R^3$, $R^4$, $R^5$, $R^6$, $R^7$, and $R^8$ may be the same or different and are independently selected from H, Cl, Br, F, I, —NO$_2$, —CN, —OH, —OR$^{15}$ groups, —NR$^{16}$R$^{17}$ groups, —C(=O)R$^{18}$ groups, —SH, —SR$^{19}$ groups, —S(=O)R$^{20}$ groups, S(=O)$_2$R$^{21}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups, and $R^1$ is absent or H if $W^1$ is N, $R^2$ is absent or H if $W^2$ is N, $R^3$ is absent or H if $W^3$ is N, $R^4$ is absent or H if $W^4$ is N, $R^5$ is absent or H if $X^1$ is N, $R^6$ is absent or H if $X^2$ is N, $R^7$ is absent or H if $X^3$ is N, and $R^8$ is absent or H if $X^4$ is N.

Some preferred compounds have the structure III where at least one of $R^1$, $R^2$, $R^3$, $R^4$, $R^5$, $R^6$, $R^7$, or $R^8$ is a substituted or unsubstituted heterocyclyl group selected from a group of heterocycles that includes morpholine, piperazine, piperidine, 1,2,3-triazole, 1,2,4-triazole, tetrazole, pyrrolidine, pyrazole, pyrrole, thiomorpholine, homopiperazine, benzimidazole, oxazolidin-2-one, pyrrolidin-2-one, imidazole, isothiazole, thiazole, thiophene, furan, pyran, tetrahydrothiophene, tetrahydrofuran, tetrahydropyran, and pyridine.

Still other preferred compounds having structure III are those in which $R^1$, $R^2$, and $R^3$ are H, and $W^4$ is N. Still other compounds having the formula of structure III are provided in which $R^2$, $R^3$, and $R^4$ are H, and $W^1$ is N. Still other compounds having the formula of structure III are provided in which $R^1$, $R^3$, and $R^4$ are H, and $W^2$ is N. Still other compounds having the formula of structure III are provided in which $R^1$, $R^2$, and $R^4$ are H, and $W^3$ is N.

In other preferred compounds, $R^1$ or $R^2$ is selected from F, Cl, substituted or unsubstituted alkoxy groups, substituted or unsubstituted heterocyclyloxy groups, substituted or unsubstituted heterocyclylalkoxy groups, substituted or unsubstituted heterocyclyl groups, substituted or unsubstituted alkyl-, heterocyclyl-, or aryl-aminoalkyl groups, substituted or unsubstituted dialkyl- or diaryl-aminoalkyl groups, substituted or unsubstituted alkylarylaminoalkyl groups, substituted or unsubstituted alkyl- and aryl-aminoalkoxy groups, substituted or unsubstituted dialkyl- and diaryl-aminoalkoxy groups, or substituted or unsubstituted alkylarylaminoalkoxy groups. Particular examples include: —C(=O)N(alkyl)$_2$ groups, —OCH$_2$CH$_2$(N-morpholinyl), N-morpholinyl, —OCH$_2$CH$_2$N(alkyl)$_2$ groups, —OCH$_2$CH$_2$NH(alkyl) groups, —OCH$_2$CH$_2$NH$_2$, —OCH$_2$CH$_2$NH(aryl) groups, —OCH$_2$CH$_2$N(aryl)$_2$ groups, alkoxy groups, —OCH$_2$CH$_2$N(alkyl)(aryl) groups, —O(4-piperidinyl), —O[4-(1-alkyl)piperidinyl] groups, —OCH$_2$(2-pyridyl), —O(3-pyrrolidinyl), or —O[3-(1-alkyl)pyrrolidinyl] groups.

Still other preferred compounds include those in which R$^2$ is selected from F, Cl, —NO$_2$, substituted or unsubstituted alkoxy groups, substituted or unsubstituted heterocyclylalkoxy groups, substituted or unsubstituted heterocyclyl groups, substituted or unsubstituted alkyl-, heterocycyl-, or aryl-aminoalkyl groups, substituted or unsubstituted dialkyl- and diaryl-aminoalkyl groups, substituted or unsubstituted alkylarylaminoalkyl groups, substituted or unsubstituted alkyl- and aryl-aminoalkoxy groups, substituted or unsubstituted dialkyl- and diaryl-aminoalkoxy groups, substituted or unsubstituted alkylarylaminoalkoxy groups. Particular examples include: —OCH$_3$, N-morpholinyl, —N-cis-dialkylmorpholinyl, —N-(4-alkyl)piperazinyl, or —OCH$_2$(2-pyridyl).

In yet preferred compounds having structure III, R$^5$, R$^6$, and R$^7$ are hydrogen, and X$^4$ is N. In still other more preferred compounds of structure III, R$^6$, R$^7$ or both R$^6$ and R$^7$ are alkyl groups having from one to four carbon atoms. In yet other preferred compounds of structure III, R$^6$ or R$^7$ is an —OR$^{15}$ group and R$^{15}$ is an alkyl, aryl, heterocyclyl, or heterocyclylalkyl group. In still further preferred compounds of structure III, R$^6$ or R$^7$ is a —OCH$_2$(CH$_2$)$_q$(heterocyclyl) group and q is 0, 1, 2, 3, or 4. In more preferred compounds in which R$^6$ or R$^7$ is a —OCH$_2$(CH$_2$)$_q$-(heterocyclyl) group, the heterocyclyl group of the —OCH$_2$(CH$_2$)$_n$(heterocyclyl) group is a heterocycle selected from substituted or unsubstituted morpholine, substituted or unsubstituted piperazine, substituted or unsubstituted piperidine, substituted or unsubstituted pyrrolidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted furan, substituted or unsubstituted thiophene, substituted or unsubstituted tetrahydrofuran, substituted or unsubstituted tetrahydrothiophene, substituted or unsubstituted benzimidazole, substituted or unsubstituted benzoxazole, or substituted or unsubstituted benzothiazole.

In compounds of structure III, R$^9$ is selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups. One group of particularly preferred compounds of structure III are those in which R$^9$ is hydrogen.

In compounds of structure III, R$^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

In compounds of structure III, R$^{11}$ and R$^{19}$ may be the same or different and are independently selected from substituted or unsubstituted alkyl groups, or substituted or unsubstituted aryl groups whereas R$^{12}$ is selected from H, substituted or unsubstituted alkyl groups, substituted or unsubstituted aryl groups, or substituted or unsubstituted heterocyclyl groups.

In compounds of structure III, R$^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. R$^{12}$ and R$^{13}$ may join together to form a 5 to 7 membered saturated or unsaturated, substituted or unsubstituted N-containing ring.

In compounds of structure III, R$^{14}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups.

In compounds of structure III, R$^{15}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)-heterocyclyl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)NH-heterocyclyl groups, —C(=O)N-(heterocyclyl)$_2$ groups, —C(=O)N(alkyl)(heterocyclyl) groups, —C(=O)N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups.

In compounds of structure III, $R^{16}$ is selected from H, substituted or unsubstituted alkyl groups, substituted or unsubstituted aryl groups, or substituted or unsubstituted heterocyclyl groups whereas $R^{17}$ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (aryl)(alkyl)aminoalkyl groups, substituted or unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. $R^{16}$ and $R^{17}$ may join together to form a 5 to 7 membered saturated or unsaturated, substituted or unsubstituted N-containing ring.

Finally, in compounds of structure III, $R^{18}$, $R^{20}$, and $R^{21}$ may be the same or different and are independently selected H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups.

Preferred compounds having the structure III include those in which $R^{18}$ is selected from substituted or unsubstituted alkyl groups, substituted or unsubstituted aryl groups, —NH$_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, or N-containing heterocycles, and the N-containing heterocycles are bonded to the carbonyl carbon of the —C(=O)—R$^{18}$ group through either a nitrogen atom or a carbon atom in the rings of the N-containing heterocycles. In still more preferred compounds in which $R^{18}$ is a N-containing heterocycle, the N-containing heterocycle of the $R^{18}$ group is selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Other preferred compounds having structure III are provided in which $R^{15}$ or $R^{17}$ is selected from substituted or unsubstituted aminoalkyl groups, substituted or unsubstituted alkylaminoalkyl groups, substituted or unsubstituted arylaminoalkyl groups, substituted or unsubstituted dialkylaminoalkyl groups, substituted or unsubstituted diarylaminoalkyl groups, alkylarylaminoalkyl groups, or substituted or unsubstituted heterocycyalkyl groups, including: —CH$_2$(CH$_2$)$_p$NH$_2$ groups, —CH$_2$(CH$_2$)$_p$NH(alkyl) groups, —CH$_2$(CH$_2$)$_p$NH(aryl) groups, —CH$_2$(CH$_2$)$_p$N(alkyl)$_2$ groups, —CH$_2$(CH$_2$)$_p$N(aryl)$_2$ groups, —CH$_2$(CH$_2$)$_p$N(alkyl)(aryl) groups, or —CH$_2$(CH$_2$)$_p$(heterocyclyl) groups, where p is an integer ranging from 0 to 4 and the heterocyclyl group of the —CH$_2$(CH$_2$)$_p$(heterocyclyl) group is a N-containing heterocycle selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Compounds of structure I and structure II may be synthesized from simple starting molecules as shown in Schemes 1–3 and exemplified in the Examples. As shown in Scheme 1, compounds of structure I and II may generally be prepared using pyridines or other heterocycles substituted with amines and carboxylic acid groups.

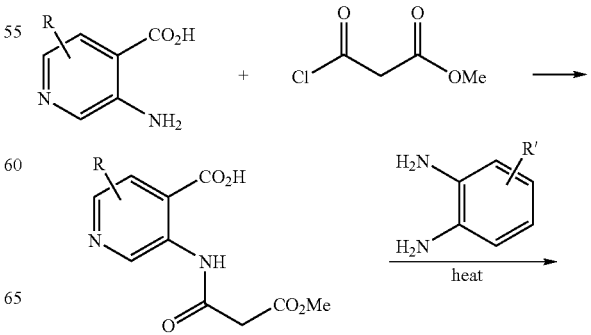

Scheme 1.

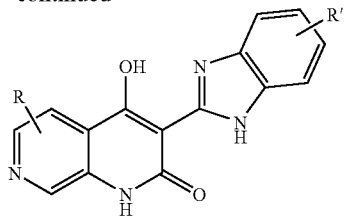

As shown in Scheme 1, a substituted pyridine such as a substituted or unsubstituted 3-amino-pyridine-4-carboxylic acid may be reacted with an acyl halide such as methyl 2-(chlorocarbonyl)acetate to produce an amide that will react with a substituted or unsubstituted 1,2-diaminobenzene. The resulting product is a 4-hydroxy-substituted compound of structure I or II. The use of starting pyridines with different substitution patterns such as 2-aminonicotinic acid (2-aminopyridine-4-carboxylic acid) provides compounds where the nitrogen is in a different position in the pyridine ring of the final compound. One skilled in the art will recognize that the procedure set forth in Scheme 1 may be modified to produce various compounds.

A method for preparing 4-amino substituted compounds of structures I and II is shown in Scheme 2.

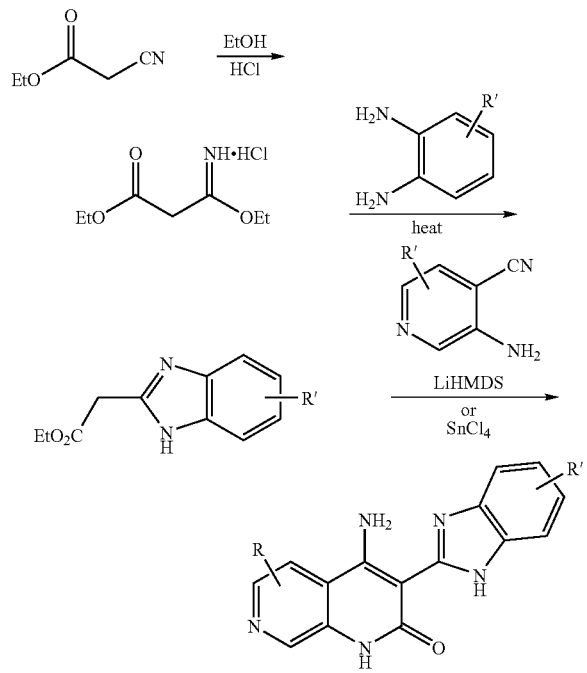

As shown in Scheme 2, pyridines and other heterocycles substituted with amine and nitrile groups may be used to synthesize 4-amino substituted compounds of Structure I and II. A compound such as ethyl 2-cyanoacetate may be reacted with ethanol to produce ethyl 3-ethoxy-3-iminopropanoate hydrochloride. Subsequent reaction with a substituted or unsubstituted 1,2-phenylenediamine provides substituted or unsubstituted ethyl 2-benzimidazol-2-ylacetate. Reaction of a substituted or unsubstituted ethyl 3 benzimidazol-2-ylacetate with a pyridine having an amine and nitrile group such as substituted or unsubstituted 3-amino-4-cyanopyridine with a base such as lithium bis(trimethylsilyl) amide or a Lewis acid such as tin tetrachloride provides the substituted or unsubstituted 4-amino substituted compound of structure I and II.

Scheme 3 illustrates a general synthetic route that allows for the synthesis of 4-dialkylamino and 4-alkylamino compounds of structures I and II. An inspection of Scheme 3 shows that 4-hydroxy substituted compounds of structure I or II may be converted into the 4-chloro derivative by reaction with phosphorous oxychloride. The 4-chloro derivative may then be reacted with an alkylamine or dialkylamine to produce the corresponding 4-alkylamino or 4-dialkylamino derivative. Deprotection affords the final 4-alkylamino or 4-dialkylamino compounds of structure I and II. Other groups that may be reacted with the 4-chloro derivative in this manner include, but are not limited to, ROH, RSH, and CuCN.

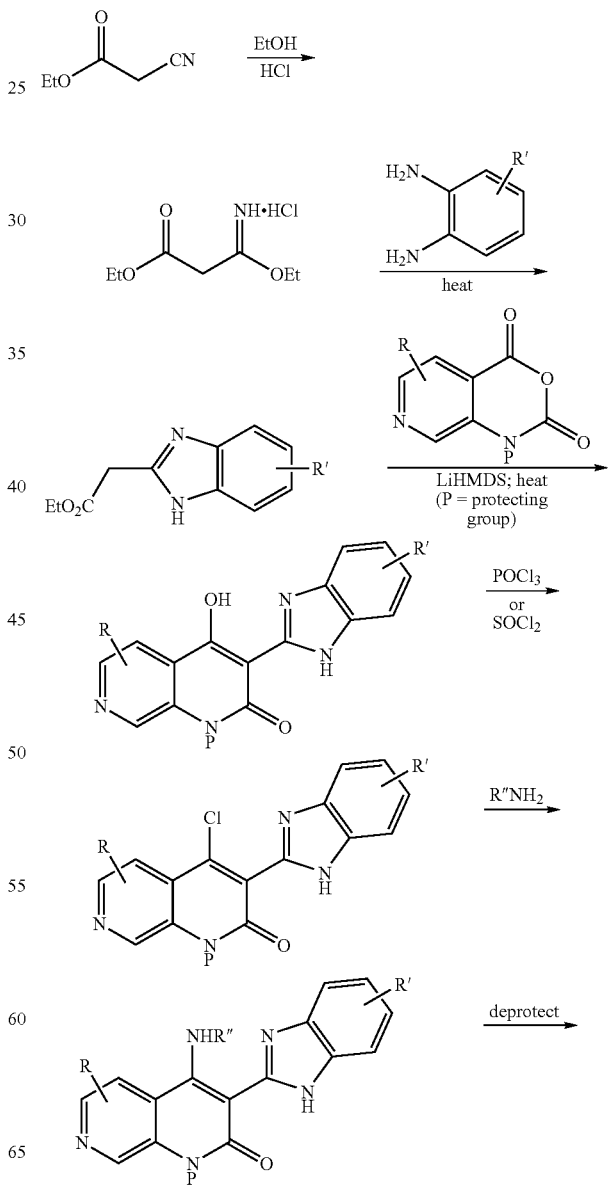

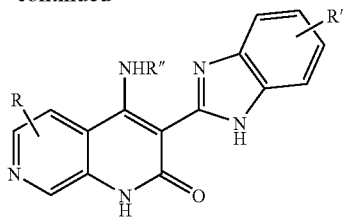

Heteroaromatic diamines may be used as precursors of compounds of structure III. The synthesis of compounds of structure III where Y=NH₂ is depicted in Scheme 4.

quently be reduced to diamines. The alcohol moiety of a nitroamino phenol may be modified using known methods to introduce a broad range of substituents into a diamine for subsequent inclusion in compound of the invention.

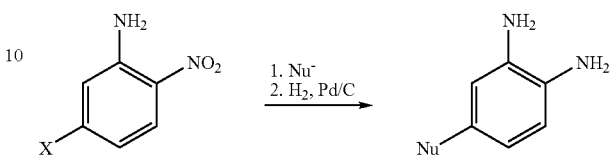

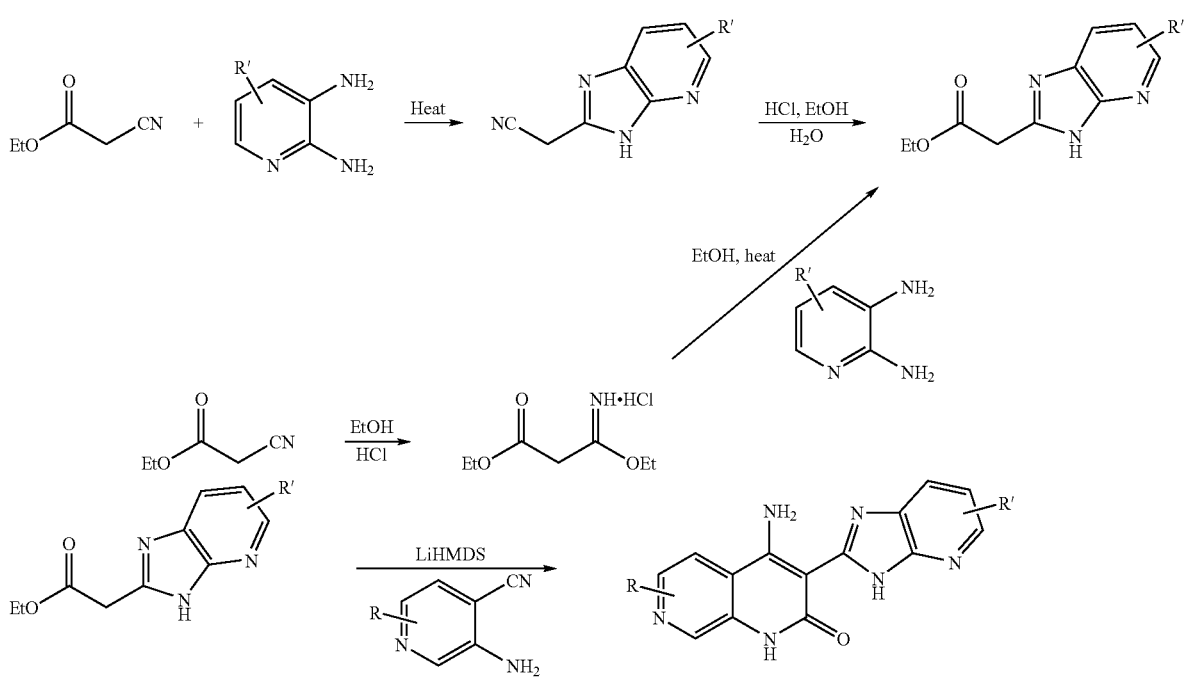

A compound such as ethyl cyanoacetate may be condensed with a substituted or unsubstituted heterocycle containing two ortho amino groups such as a substituted or unsubstituted 1,2-diaminopyridine to obtain a substituted or unsubstituted 2-imidazolo[5,4-b]pyridin-2-ylethanenitrile, which may be hydrolyzed in acidic medium to provide a substituted or unsubstituted ethyl 2-imidazolo[5,4-b]pyridin-2-ylacetate. As an alternate route, a substituted or unsubstituted ethyl 2-imidazolo[5,4-b]pyridin-2-ylacetate may be obtained from a compound such as the hydrochloride salt of 3-ethoxy-3-iminopropanoate and a substituted or unsubtituted 1,2-diaminopyridine. Reaction of a substituted or unsubstituted ethyl 2-imidazolo[5,4-b]pyridin-2-ylacetates with a pyridine having an amine and nitrile group such as a substituted or unsubstituted 3-amino-4-cyanopyridine and a base such as lithium bis(trimethylsilyl)amide provides the substituted or unsubstituted compound of structure III.

Scheme 5 illustrates just a few of the methods that may be used to produce a variety of 2-amino anilines. Halo (X=halogen) nitroanilines may be reacted with a wide variety of nucleophiles (Nu⁻) such as alcohols and amines to produce functionalized nitroanilines which may subse-

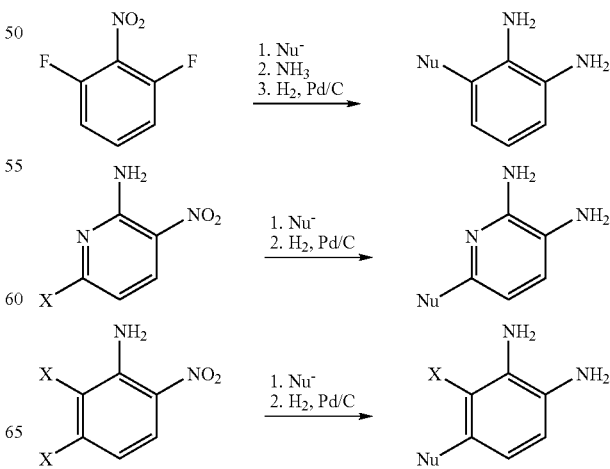

-continued

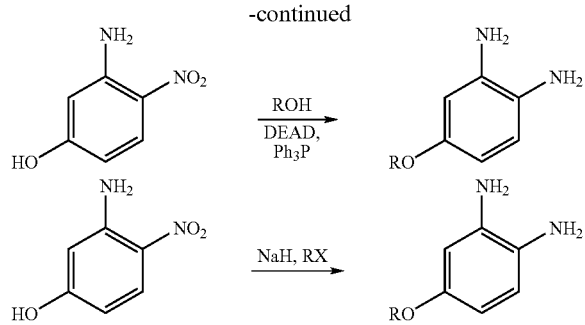

The instant invention also provides for compositions which may be prepared by mixing one or more compounds of the instant invention, or pharmaceutically acceptable salts or tautomers thereof, with pharmaceutically acceptable carriers, excipients, binders, diluents or the like to treat or ameliorate a variety of disorders related to the activity of VEGF-RTK, more particularly angiogenesis associated with cancer. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations may be a spray or aerosol containing and appropriate solvents and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of VEGF-RTK, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anticancer drugs including those used in antisense and gene therapy. Examples of standard chemotherapeutic agents that the compounds of the present may be used with include, but are not limited to, cisplatin, taxol, and 5-fluorouracil.

Pharmaceutical formulations according to the invention include any of the compounds described above in combination with a pharmaceutically acceptable carrier.

A method of treating a patient in need of an inhibitor of vascular endothelial growth factor receptor tyrosine kinase includes administering an effective amount of a pharmaceutical formulation according to the invention to a patient in need thereof.

A method for inhibiting tumor growth in a patient includes administering an effective amount of the compound or a pharmaceutically acceptable salt thereof to a patient having a tumor.

A method for inhibiting the proliferation of capillaries in a patient includes administering an effective amount of the compound or a pharmaceutically acceptable salt thereof according to a patient in need.

A method of preparing pharmaceutical formulations includes mixing any of the above-described compounds with a pharmaceutically acceptable carrier and water or an aqueous solution.

The present invention, thus generally described, will be understood more readily by reference to the following examples, which are provided by way of illustration and are not intended to be limiting of the present invention.

EXAMPLES

The following abbreviations are used throughout the Examples:

| | |
|---|---|
| ATP: | Adenosine triphosphate |
| BSA: | Bovine Serum Albumin |
| DMSO: | Dimethylsulfoxide |
| DTT: | DL-Dithiothreitol |
| EDTA: | Ethylene diamine tetraacetic acid |
| EtOAc: | Ethyl acetate |
| EtOH: | Ethanol |
| HBTU: | O-Benzotriazol-1-yl-N,N,N',N'-tetramethyluronium hexafluorophosphate |
| $IC_{50}$ value: | The concentration of an inhibitor that causes a 50 percent reduction in a measured activity |
| LiHMDS: | Lithium bis(trimethylsilyl)amide |
| MeOH: | Methanol |
| NaOH: | Sodium hydroxide |
| NaOMe: | Sodium methoxide |
| NMP: | N-methylpyrrolidone |
| TFA: | Trifluoroacetic acid |
| THF: | Tetrahydrofuran |

Various functionalized aryl diamines were obtained from commercial sources, prepared by methods know to those of skilled in the art, or were prepared by the following general methods. The compounds were named using Nomenclator (v. 3.0 & v. 5.0) from Cmemlnovation Software, Inc. and ACD/Name v. 4.53.

The various aryl diamine starting materials used to synthesize benzimidazole acetates may be obtained from commercial sources, prepared by methods know to one of skill in the art, or prepared by the following general methods 1–7.

Method 1

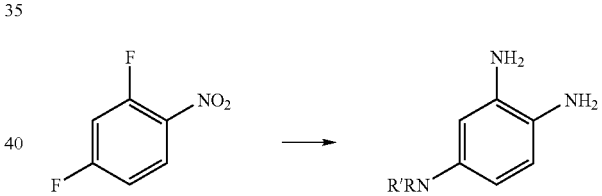

2,4-Difluoronitrobenzene (1.0 eq) was placed in a dry round-bottomed flask equipped with a dry ice condenser charged with acetone and dry ice. Ammonia was condensed into the flask and the resulting solution was stirred at reflux for 7 hours. A yellow precipitate formed within 1 hour. After 7 hours, the condenser was removed and the liquid ammonia was allowed to evaporate over several hours. The crude product was purified by flash chromatography on silica gel (85:15 hexanes:ethyl acetate, product at $R_f$=0.32, contaminant at $R_f$=0.51); GC/MS m/z 156.1 (M+), $R_t$ 11.16 minutes.

The resulting 5-fluoro-2-nitrophenylamine (1.0 eq) and an amine (1.1 eq) e.g. N-methyl piperazine, were dissolved in NMP and triethylamine (2.0 eq) was added. The reaction mixture was heated at 100° C. for 3 hours. The solution was then cooled to room temperature and diluted with water. The resulting precipitate was filtered and dried under vacuum to provide the 2-nitro-diamino product. Alternatively, the same product may be obtained from commercially available 5-chloro-2-nitrophenylamine under identical conditions except heating at 130° C. for 1–2 days. In some examples, the displacement on either 5-fluoro-2-nitrophenylamine or 5-chloro-2-nitrophenylamine can be conducted in neat amine (5 eq) at 100° C. or 130° C., respectively. The product is isolated in an identical manner. LC/MS m/z 237.1 (MH+), $R_t$ 1.304 minutes.

The nitroamine (1.0 eq) and 10% Pd/C (0.1 eq) was suspended in anhydrous ethanol at room temperature. The reaction flask was evacuated and subsequently filled with $H_2$. The resulting mixture was then stirred under a hydrogen atmosphere overnight. The resulting solution was filtered through Celite and concentrated under vacuum to provide the crude product which was used without further purification.

Method 2

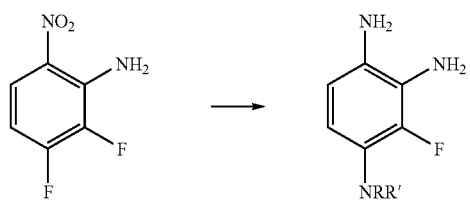

A round-bottom flask was charged with 2,3-difluoro-6-nitrophenylamine (1 eq) and enough NMP to make a viscous slurry. An amine (5 eq), e.g. N-methyl piperazine, was added and the solution was heated at 100° C. After 2 hours, the solution was cooled and poured into water. A bright yellow solid formed which was filtered and dried. The nitroamine was reduced as in Method 1 to provide the crude product which was used without further purification. LC/MS m/z 225.1 (MH+), $R_t$ 0.335 minutes.

Method 3

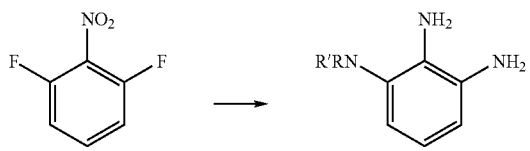

To a 0.1 M DMF solution of 1,3-difluoro-2-nitrobenzene was added $Et_3N$ (2 eq) followed by an amine (1 eq), e.g. morpholine. The mixture was stirred for 18 hours and then diluted with water and extracted with ethyl acetate. LC/MS m/z 227.2 (MH+), $R_t$ 2.522 minutes. The combined organic layers were dried over $MgSO_4$, filtered, and concentrated. Ammonia was condensed into a bomb containing the crude product. The bomb was sealed and heated to 100° C. (over 400 psi). After 72 hours the bomb was allowed to cool and the ammonia was evaporated to provide a reddish solid. The nitroamine was reduced as in Method 1 to provide the crude product which was used without further purification. LC/MS m/z 194.1 (MH+), $R_t$ 1.199 minutes.

Method 4

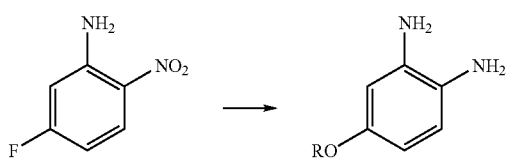

To a stirred NMP solution containing NaH (1.3 eq) was added an alcohol (1.0 eq), e.g. 2-methyloxyethanol. The resulting mixture was then stirred for 30 minutes. A slurry of 5-fluoro-2-nitrophenylamine in NMP was then added slowly. The mixture was then heated to 100° C. After 2 hours, the reaction mixture was cooled and water was added. The mixture was then filtered and the captured solid was washed with water and purified by silica gel chromatography (1:1 ethyl acetate:hexane). LC/MS m/z 213.2 (MH+), $R_t$ 2.24 minutes. The nitroamine was reduced as in Method 1 to provide the crude product which was used without further purification. LC/MS m/z 183.1 (MH+), $R_t$ 0.984 minutes.

Method 5

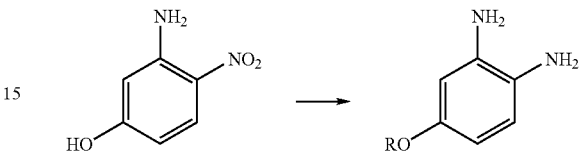

Diisopropyl azodicarboxylate (1.1 eq) was added dropwise to a stirred solution of 4-amino-3-nitrophenol (1.0 eq), triphenylphosphine (1.1 eq), and an alcohol, e.g. N-(2-hydroxyethyl)morpholine (1.0 eq), in tetrahydrofuran at 0° C. The mixture was allowed to warm to room temperature and stirred for 18 hours. The solvent was evaporated, and the product was purified by silica gel chromatography (98:2 $CH_2Cl_2$:methanol) to yield 4-(2-morpholin-4-ylethoxy)-2-nitrophenylamine as a dark reddish-brown oil. LC/MS m/z 268.0 (MH+), $R_t$ 1.01 minutes. The nitroamine was reduced as in Method 1 to give the crude product which was used without further purification. LC/MS m/z 238.3 (MH+), $R_t$ 0.295 minutes.

Method 6

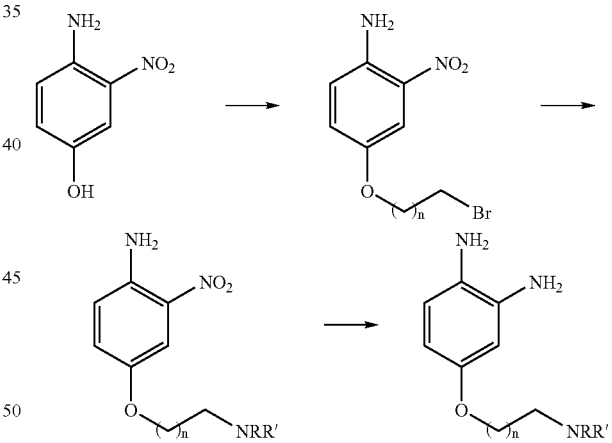

To a flask charged with 4-amino-3-nitrophenol (1 eq), $K_2CO_3$ (2 eq), and 2-butanone was added an alkyl dibromide, e.g. 1,3-dibromopropane (1.5 eq). The resulting mixture was then heated at 80° C. for 18 hours. After cooling, the mixture was filtered, concentrated, and diluted with water. The solution was then extracted with $CH_2Cl_2$ (3×) and the combined organic layers were concentrated to give a solid that was then washed with pentane. LCMS m/z 275.1 (MH+), $R_t$ 2.74 minutes.

An acetonitrile solution of the bromide prepared above, an amine, e.g. pyrrolidine (5 eq), $Cs_2CO_3$ (2 eq) and $Bu_4NI$ (0.1 eq) was heated at 70° C. for 48 hours. The reaction mixture was cooled, filtered, and concentrated. The residue was dissolved in $CH_2Cl_2$, washed with water, and concentrated to give the desired nitroamine, 2-nitro-4-(3-pyrrolidin-1-ylpropoxy)phenylamine. LCMS m/z 266.2 (MH+), $R_t$ 1.51 minutes. The nitroamine was reduced as in Method 1 to provide the crude product which was used without further purification.

Method 7

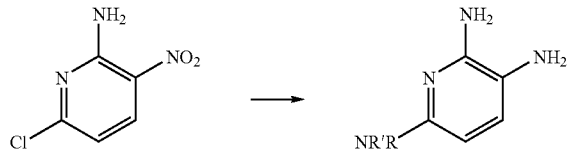

To a suspension of 6-chloro-3-nitropyridin-2-amine (1 eq) in acetonitrile was added an amine, e.g. morpholine (4 eq). The resulting reaction mixture was stirred at 70° C. for 5 hours. The solvent was evaporated under reduced pressure, and the residue triturated with ether to provide the desired compound as a bright yellow powder. LC/MS m/z 225.0 (MH+), $R_t$ 1.79 minutes. The nitroamine was reduced as in Method 1 to provide the crude product which was used without further purification.

Example 1

3-[2-(Methoxycarbonyl)acetylamino]pyridine-4-carboxylic acid

A solution of 3-aminopyridine-4-carboxylic acid (1.0 eq), methyl 2-(chlorocarbonyl)acetate (1.1 eq), and triethylamine (2.0 eq) in acetone was stirred overnight at room temperature. The solvent was removed in vacuo. The product was used without further purification. LC/MS m/z 239.2 (MH+), $R_t$ 1.40 minutes.

3-Benzimidazol-2-yl-4-hydroxyhydropyridino[3,4-b]pyridin-2-one

3-[2-(Methoxycarbonyl)acetylamino]pyridine-4-carboxylic acid (1.1 eq) was combined with 1,2-phenylenediamine (1.0 eq) and heated at 150° C. for 3 hours. The crude product was purified by reversed-phase HPLC (DMSO/5% TFA). LC/MS m/z 279.3 (MH+), $R_t$ 1.73 minutes.

Example 2

4-Hydroxy-3-(5-methylbenzimidazol-2-yl)hydropyridino[3,4-b]pyridin-2-one

The title compound was synthesized as described in Example 1 using 3-[2-(methoxycarbonyl)acetylamino]-pyridine-4-carboxylic acid and 4-methyl-1,2-phenylenediamine. The crude product was purified by reversed-phase HPLC (DMSO/5% TFA). LC/MS m/z 293.3 (MH+), $R_t$ 1.99 minutes.

Example 3

Ethyl 2-benzimidazol-2-ylacetate

A solution of 1,2-phenylenediamine (1.0 eq) and ethyl 3-ethoxy-3-iminopropanoate hydrochloride (1.3 eq) in EtOH was stirred at 90° C. overnight. The reaction was cooled to room temperature and the solvent removed in vacuo. Water and $CH_2Cl_2$ were added to the residue. The organic layer was separated, dried over $Na_2SO_4$ and the solvent removed. The solid recovered was used without purification. LC/MS m/z 205.2 (MH+), $R_t$ 1.44 minutes.

Method A

2-Benzimidazol-2-yl-N-(4-cyano(3-pyridyl))acetamide

LiHMDS (2.5 eq) was added to ethyl 2-benzimidazol-2-ylacetate (1.0 eq) in THF at −78° C. After 1 hour, 3-amino-4-cyanopyridine (0.8 eq) in THF was added. The resulting mixture was allowed to warm to room temperature overnight. The mixture was quenched with $NH_4Cl$ (aqueous saturated solution) and extracted with EtOAc. The organic layer washed with $H_2O$ and brine, dried over $Na_2SO_4$, filtered, and concentrated in vacuo to yield a brown solid. The crude material was purified by silica gel chromatography (5:1 EtOAc:hexane) to yield the desired product. LC/MS m/z 278.3 (MH+), $R_t$ 1.88 minutes.

4-Amino-3-benzimidazol-2-ylhydropyridino[3,4-b]pyridin-2-one

2-Benzimidazol-2-yl-N-(4-cyano(3-pyridyl))acetamide (1.0 eq) was heated in NaOMe (18 eq, 0.5 M in MeOH) at 70° C. for 2 hours. The reaction mixture was cooled, and the resulting solid was filtered and washed with water to provide the desired product. LC/MS m/z 278.3 (MH+), $R_t$ 1.91 minutes.

Example 4

Ethyl 2-(5-methylbenzimidazol-2-yl)acetate

The title compound was synthesized as described in Example 3 using 4-methyl-1,2-phenylenediamine. LC/MS m/z 219.3 (MH+), $R_t$ 1.60 minutes.

N-(4-Cyano(3-pyridyl))-2-(5-methylbenzimidazol-2-yl)acetamide

The title compound was synthesized as described in Example 3, Method A using ethyl 2-(5-methylbenzimidazol-2-yl)acetate. LC/MS m/z 292.4 (MH+), $R_t$ 1.71 minutes.

4-Amino-3-(5-methylbenzimidazol-2-yl)hydropyridino[3,4-b]pyridin-2-one

The title compound was synthesized as described in Example 3, Method A using N-(4-cyano(3-pyridyl))-2-(5-methylbenzimidazol-2-yl)acetamide. LC/MS m/z 292.4 (MH+), $R_t$ 2.04 minutes.

Example 5

4-(2-Morpholin-4-ylethoxy)-2-nitrophenylamine

Diisopropyl azodicarboxylate (1.1 eq) was added dropwise to a stirred solution of 4-amino-3-nitrophenol (1.0 eq), triphenylphosphine (1.1 eq), and N-(2-hydroxyethyl)morpholine (1.0 eq), in THF at 0° C. The mixture was allowed to warm to room temperature and left to stir for 18 hours. The solvent was evaporated and the product was purified by silica gel chromatography (98:2 $CH_2Cl_2$:MeOH) to yield a dark reddish-brown oil. LC/MS m/z 268.0 (MH+), $R_t$ 1.01 minutes.

4-(2-Morpholin-4-ylethoxy)benzene-1,2-diamine

To a solution 4-(2-morpholin-4-ylethoxy)-2-nitrophenylamine (1.0 eq) in EtOH was added Pd/C (0.1 eq). The reaction vessel was repeatedly purged with nitrogen, then stirred under a hydrogen atmosphere (1 atm) for 18 hours. The product was filtered through a Celite plug, and the plug washed with EtOH. The diamine was used without purification. LC/MS m/z 238.3 (MH+), $R_t$ 0.295 minutes.

Ethyl 2-[5-(2-morpholin-4-ylethoxy)benzimidazol-2-yl]acetate

The title compound was synthesized as described in Example 3 using 4-(2-morpholin-4-ylethoxy)benzene-1,2-diamine; The organic layer was concentrated and the residue purified by silica gel chromatography (10:1:2 $CH_2Cl_2$:MeOH:EtOAc) to yield a dark reddish brown oil. LC/MS m/z 334.4 (MH+), $R_t$ 1.08 minutes.

N-(4-Cyano(3-pyridyl))-2-[5-(2-morpholin-4-ylethoxy)benzimidazol-2-yl]acetamide The title compound was synthesized as described in Example 3, Method A using ethyl 2-[5-(2-morpholin-4-ylethoxy)benzimidazol-2-yl]acetate. LC/MS m/z 407.4 (MH+), $R_t$ 1.25 minutes.

4-Amino-3-[5-(2-morpholin-4-ylethoxy)benzimidazol-2-yl]hydropyridino[3,4-b]pyridin-2-one The title compound was synthesized as described in Example 3, Method A using N-(4-cyano(3-pyridyl))-2-[5-(2-morpholin-4-ylethoxy)benzimidazol-2-yl]acetamide. LC/MS m/z 407.4 (MH+), $R_t$ 1.41 minutes.

Example 6

2-[(Ethoxycarbonyl)methyl]benzimidazole-5-carboxylic Acid

The title compound was synthesized as described in Example 3 using 3,4-diaminobenzoic acid. The crude material was purified by silica gel chromatography (0–5% MeOH/$CH_2Cl_2$) to afford the desired product as a white to off-white solid. LC/MS m/z 249.1 (MH+), $R_t$ 1.35 minutes.

Ethyl 2-[5-(N,N-dimethylcarbamoyl)benzimidazol-2-yl]acetate

2-[(Ethoxycarbonyl)methyl]benzimidazole-5-carboxylic acid (1.0 eq) was dissolved in THF. HBTU (1.1 eq) and diisopropylethylamine (2.0 eq) were added, followed by dimethylamine (2.0 M in THF, 1.1 eq). The reaction was stirred at room temperature overnight then concentrated and the residue was purified by silica gel chromatography (5:95 MeOH/$CH_2Cl_2$) to afford the desired compound. LC/MS m/z 276.2 (MH+), $R_t$ 1.18 minutes.

Method B

[2-(4-Amino-2-oxohydropyridino[3,4-b]pyridin-3-yl)benzimidazol-5-yl]-N,N-dimethylcarboxamide Ethyl 2-[5-(N,N-dimethylcarbamoyl)benzimidazol-2-yl]acetate (1.0 eq) and anthranilonitrile (1.0 eq) were dissolved in 1,2-dichloroethane, and then $SnCl_4$ (5.5 eq) was added. The mixture was heated at reflux overnight. Upon cooling, the mixture was concentrated in vacuo. NaOH (3 M) was added to the solid, and the mixture heated at 80° C. for 0.5 hours. The solid was filtered and washed sequentially with $H_2O$, $CH_2Cl_2$, and acetone. LC/MS indicated that the product was present in the acetone layer and the solid. These fractions were combined and purified by silica gel chromatography (5–10% MeOH in $CH_2Cl_2$ with 1% $Et_3N$) to give the desired product. LC/MS m/z 349.3 (MH+), $R_t$ 1.68 minutes.

Example 7

5-Fluoro-2-nitrophenylamine 2,4-Difluoronitrobenzene (1.0 eq) was placed in a dry round-bottomed flask equipped with a dry ice condenser charged with acetone/dry ice. Ammonia was condensed into the flask and the resulting solution was stirred at reflux for 7 hours. A yellow precipitate was formed within 1 hour. After 7 hours, the condenser was removed and the liquid ammonia was allowed to evaporate over several hours. The crude product was purified by flash chromatography on silica gel (85:15 hexanes:EtOAc, product at $R_f$=0.32, contaminant at $R_f$=0.51). GC/MS m/z 156.1 (M+), $R_t$ 11.16 minutes.

5-Morpholin-4-yl-2-nitrophenylamine

5-Fluoro-2-nitrophenylamine (1.0 eq) and morpholine (3.0 eq) were dissolved in NMP and heated at 100° C. for 1 hour. The solution was cooled to room temperature and diluted with water. The resulting precipitate was filtered and dried under vacuum to yield 5-morpholin-4-yl-2-nitrophenylamine. The resulting solid was recrystallized from EtOH to afford pure product as a bright yellow solid. LC/MS m/z 224.1 (MH+), $R_t$ 1.89 minutes.

Ethyl 2-(5-morpholin-4-ylbenzimidazol-2-yl)acetate

The title compound was synthesized as described in Example 5 using 5-morpholin-4-yl-2-nitrophenylamine. The crude yellow oil was purified by flash column chromatography (89.5:10:0.5 $CH_2Cl_2$:MeOH:$Et_3N$) to yield pure product as a yellow solid. LC/MS m/z 290.3 (MH+), $R_t$ 1.31 minutes.

4-Amino-3-(5-morpholin-4-ylbenzimidazol-2-yl)hydropyridino[3,4-b]pyridin-2-one The title compound was synthesized as described in Example 6, Method B using ethyl 2-(5-morpholin-4-ylbenzimidazol-2-yl)acetate. LC/MS m/z 363.2 (MH+), $R_t$ 1.60 minutes.

Example 8

[1-(3-Amino-4-nitrophenyl)pyrrolidin-3-yl]dimethylamine

The title compound was synthesized as described in Example 7 using 3-(dimethylamino)pyrrolidine. LC/MS m/z 251.3 (MH+), $R_t$ 1.25 minutes.

Ethyl 2-{5-[3-(dimethylamino)pyrrolidinyl]benzimidazol-2-yl}acetate

The title compound was synthesized as described in Example 5 using [1-(3-amino-4-nitrophenyl)pyrrolidin-3-yl]dimethylamine and the resulting diamine was used according to Example 3 to form the benzimidazole. The product was obtained as a yellow oil. LC/MS m/z 317.4 (MH+), $R_t$ 1.36 minutes.

4-Amino-3-{5-[3-(dimethylamino)pyrrolidinyl]benz-
imidazol-2-yl)hydropyridino[3,4-b]pyridin-2-one The title compound was synthesized as described in Example 6, Method B using ethyl 2-[5-(dimethylamino) benzimidazol-2-yl]acetate. LC/MS m/z 390.2 (MH+), $R_t$ 1.45 minutes.

Example 9

3H-Imidazo[4,5-b]pyridin-2-ylacetonitrile

Ethyl cyanoacetate (1.5 eq) and 2,3-diaminopyridine (1 eq) were heated at 185° C. for 30 minutes. The reaction mixture was cooled to room temperature and the black solid was triturated with ether. The desired product was thus obtained as a dark brown powder. LC/MS m/z 159.1 (MH+), $R_t$ 0.44 minutes.

Ethyl 3H-imidazo[4,5-b]pyridin-2-ylacetate

3H-Imidazo[4,5-b]pyridin-2-ylacetonitrile was suspended in EtOH, and gaseous HCl was bubbled through for 3 hours. The suspension initially dissolved, but a precipitate started forming almost immediately. The reaction mixture was cooled to 0° C. and a cold saturated NaHCO$_3$ solution was carefully added. Solid NaHCO$_3$ was also added until a pH of 7.6 was achieved. The aqueous phase was then extracted with EtOAc, and the organic extracts were dried (Na$_2$SO$_4$). After evaporation of the solvent under reduced pressure, the residue was purified by chromatography on silica gel (10% MeOH in CH$_2$Cl$_2$ with 1% Et$_3$N) providing the desired product as a light brown solid. LC/MS m/z 206.1 (MH+), $R_t$ 0.97 minutes.

4-Amino-3-(3H-imidazo[4,5-b]pyridin-2-yl)-1,7-
naphthyridin-2(1H)-one

LiHMDS (3.0 eq) was added to ethyl 3H-imidazo[4,5-b]pyridin-2-ylacetate (1.0 eq) in THF at −78° C. After 20 minutes, a solution of 3-aminopyridine-4-carbonitrile (1.1 eq) in THF was added. The resulting mixture was allowed to warm to room temperature, stirred 3 hours, and then refluxed overnight. The mixture was cooled to 0° C. and quenched with an aqueous saturated NH$_4$Cl solution. A precipitate formed, was filtered off, and was washed repeatedly with ether to yield the desired compound as a brown solid. Purification by reverse phase chromatography afforded the desired product as a yellow solid. LC/MS m/z 279.0 (MH+), $R_t$ 1.29 minutes.

Example 10

4-Amino-3-[5-(4-methylpiperazin-1-yl)-1H-benzimi-
dazol-2-yl]-1,7-naphthyridin-2(1H)-one LiHMDS (3.6 eq) was added to ethyl [5-(4-methylpiperazin-1-yl)-1H-benzimidazol-2-yl]acetate (1.0 eq) and 3-aminopyridine-4-carbonitrile (1.0 eq) in THF at 0° C. The reaction was stirred overnight. The resulting mixture was quenched with an aqueous saturated NH$_4$Cl solution and extracted with EtOAc. The combined organic layers were washed with H$_2$O and brine, dried over Na$_2$SO$_4$, filtered, and concentrated in vacuo to yield a green solid. The crude material was washed successively with CH$_2$Cl$_2$ and MeOH and then was purified by reverse phase HPLC to provide the desired product. LC/MS m/z 376.3 (MH+), $R_t$ 1.70 minutes.

Example 11

4-Amino-3-(5-morpholin-4-yl-1H-benzimidazol-2-
yl)-1,6-naphthyridin-2(1H)-one

LiHMDS (3.3 eq) was added to ethyl (5-morpholin-4-yl-1H-benzimidazol-2-yl)acetate (1.0 eq) and 4-aminopyridine-3-carbonitrile (see J. Chem. Soc. 1967, p 1558–1564; 1.0 eq) in THF at 0° C. The reaction was stirred overnight. The resulting mixture was quenched with an aqueous saturated NH$_4$Cl solution and extracted with EtOAc. The combined organic layers were washed with H$_2$O and brine, dried over Na$_2$SO$_4$, filtered, and concentrated in vacuo to yield a brown solid. The crude material was washed successively with CH$_2$Cl$_2$ and MeOH, and then was purified by reverse phase HPLC to provide the desired product. LC/MS m/z 363.2 (MH+), $R_t$ 1.55 minutes.

Example 12

4-Amino-3-(5-[3-(dimethylamino)pyrrolidin-1-yl]-
1H-benzimidazol-2-yl}-1,5-naphthyridin-2(1H)-one LiHMDS (3.6 eq) was added to ethyl {5-[3-(dimethylamino)pyrrolidin-1-yl]-1H-benzimidazol-2-yl}acetate (1.0 eq) and 3-aminopyridine-2-carbonitrile (J. Org. Chem. 1958, 1616–1617; 1.0 eq) in THF at 0° C. The reaction was stirred overnight and then heated at 40° C. for 3 hours. The resulting mixture was quenched with an aqueous saturated NH$_4$Cl solution and extracted with EtOAc. The combined organic layers were washed with H$_2$O and brine, dried over Na$_2$SO$_4$, filtered, and concentrated in vacuo to yield a green solid. The crude material was washed successively with CH$_2$Cl$_2$ and MeOH, and then was purified by reverse phase HPLC to provide the desired product. LC/MS m/z 390.2 (MH+), $R_t$ 1.79 minutes.

Example 13

4-Amino-3-[5-(4-methylpiperazin-1-yl)-1H-benzimi-
dazol-2-yl]-1,5-naphthyridin-2(1H)-one LiHMDS (3.6 eq) was added to ethyl [5-(4-methylpiperazin-1-yl)-1H-benzimidazol-2-yl]acetate (1.0 eq) and 3-aminopyridine-2-carbonitrile (1.0 eq) in THF at 0° C. The reaction was stirred overnight and then heated at 40° C. for 3 hours. The resulting mixture was quenched with an aqueous saturated NH$_4$Cl solution and extracted with EtOAc. The combined organic layers were washed with H$_2$O and brine, dried over Na$_2$SO$_4$, filtered, and concentrated in vacuo to yield a green solid. The crude material was washed successively with CH$_2$Cl$_2$ and MeOH, and then was purified by reverse phase HPLC to provide the desired product. LC/MS m/z 376.1 (MH+), $R_t$ 1.50 minutes.

Example 14

3-(1H-Benzimidazol-2-yl)-4-hydroxy-1,8-naphthyri-
din-2(1H)-one

The synthesis of the title compound is outlined in Scheme 5.

Example 15

2-(1H-Benzimidazol-2-yl)-N-(4-cyano-1H-pyrazol-5-yl)acetamide

LiHMDS (4.3 eq) was added to ethyl 1H-benzimidazol-2-ylacetate (1.0 eq) 5-amino-1H-pyrazole-4-carbonitrile (1.0 eq) in THF at 0° C. After 1 hour, the resulting mixture was warmed to room temperature, stirred overnight, and then heated at 40° C. for 4 hours. The mixture was quenched with an aqueous saturated $NH_4Cl$ solution and extracted with EtOAc. The organic layer was washed with $H_2O$ and brine, dried over $Na_2SO_4$, filtered, and concentrated in vacuo to yield a tan solid. LC/MS m/z 267.1 (MH+), $R_t$ 1.37 minutes.

4-Amino-5-(1H-benzimidazol-2-yl)-1,7-dihydro-6H-pyrazolo[3,4-b]pyridin-6-one 2-(1H-Benzimidazol-2-yl)-N-(4-cyano-1H-pyrazol-5-yl)acetamide (1.0 eq) was heated in NaOMe (20 eq, 0.5 M in MeOH) at 100° C. for 2 days. $H_2O$ was added, and the mixture was extracted with EtOAc. The organic layer was washed with $H_2O$ and brine, dried over $Na_2SO_4$, filtered, and concentrated in vacuo to yield a solid. The material was purified by reverse phase HPLC. LC/MS m/z 267.1 (MH+), $R_t$ 1.57 minutes.

Example 16

4-Amino-5-(1H-benzimidazol-2-yl)thieno[2,3-b]pyridin-6(7H)-one

LiHMDS (4.3 eq) was added to ethyl 1H-benzimidazol-2-ylacetate (1.1 eq) and 2-aminothiophene-3-carbonitrile (1.0 eq) in THF at 0° C. After 1 hour, the resulting mixture was warmed to room temperature and then stirred overnight. The mixture was quenched with an aqueous saturated $NH_4Cl$ solution and extracted with EtOAc. The organic layer was washed with $H_2O$ and brine, dried over $Na_2SO_4$, filtered, and concentrated in vacuo to yield a brown solid. LC/MS m/z 283.1 (MH+), $R_t$ 1.88 minutes.

Example 17

7-Amino-6-(1H-benzimidazol-2-yl)-3,4-dihydro-5H-imidazo[4,5-b]pyridin-5-one

LiHMDS (4.4 eq) was added to ethyl 1H-benzimidazol-2-ylacetate (1.0 eq) and 5-amino-1H-imidazole-4-carbonitrile (1.0 eq) in THF at 0° C. After 1 hour, the resulting mixture was warmed to room temperature and then stirred overnight. The mixture was quenched with an aqueous saturated $NH_4Cl$ solution and extracted with EtOAc. The organic layer was washed with $H_2O$ and brine, dried over $Na_2SO_4$, filtered, and concentrated in vacuo to yield a brown solid. LC/MS m/z 267.1 (MH+), $R_t$ 1.47 minutes.

Example 18

4-Amino-5-(1H-benzimidazol-2-yl)-1-methyl-1,7-dihydro-6H-pyrazolo[3,4-b]pyridin-6-one 5-Amino-1-methyl-1H-pyrazole-4-carbonitrile (1.0 eq) and ethyl 1H-benzimidazol-2-ylacetate (1.0 eq) were dissolved in THF and dried over sieves. LiHMDS (3 eq) was added dropwise and the mixture stirred for 18 hours. The mixture was filtered and diluted with EtOAc, then washed with an aqueous saturated $NH_4Cl$ solution. The aqueous layer was washed with EtOAc (3×), and the organic layers combined, dried over $MgSO_4$, and concentrated yielding pure product. LC/MS m/z 281.0 (MH+), $R_t$ 1.41 minutes.

Assay Procedures

In Vitro Kinase Assays for Receptor Tyrosine Kinases

The kinase activity of various protein tyrosine kinases can be measured by providing ATP and a suitable peptide or protein tyrosine-containing substrate, and assaying the transfer of phosphate moiety to the tyrosine residue. Recombinant proteins corresponding to the cytoplasmic domains of the flt-1 (VEGER1), KDR (VEGFR2), and bFGF receptors were expressed in Sf9 insect cells using a Baculovirus expression system (InVitrogen) and purified via Glu antibody interaction (for Glu-epitope tagged constructs) or by Metal Ion Chromatography (for $His_6$ (SEQ ID NO: 1) tagged constructs). For each assay, test compounds were serially diluted in DMSO then mixed with an appropriate kinase reaction buffer plus ATP. Kinase protein and an appropriate biotinylated peptide substrate were added to give a final volume of 100 µL, reactions were incubated for 1–2 hours at room temperature and stopped by the addition of 50 µL of 45 mM EDTA, 50mM Hepes pH 7.5. Stopped reaction mix (75 µL) was transferred to a streptavidin coated microtiter plate (Boehringer Mannheim) and incubated for 1 hour. Phosphorylated peptide product was measured with the DELFIA time-resolved fluorescence system (Wallac), using a Eu-labeled anti-phosphotyrosine antibody PT66 with the modification that the DELFIA assay buffer was supplemented with 1 mM $MgCl_2$ for the antibody dilution. Time resolved fluorescence was read on a Wallac 1232 DELFIA fluorometer. The concentration of each compound for 50% inhibition ($IC_{50}$) was calculated by non-linear regression using XL Fit data analysis software.

Flt-1, KDR, and bFGFR kinases were assayed in 50 mM Hepes pH 7.0, 2 mM $MgCl_2$, 10 mM $MnCl_2$, 1 mM NaF, 1 mM DTT, 1 mg/ml BSA, 2 µM ATP, and 0.42 µM biotin-GGGGQDGKDYIVLPI-$NH_2$ (SEQ ID NO: 2). Flt-1, KDR, and bFGFR kinases were added at 0.1 µg/mL, 0.05 µg/mL, or 0.1 µg/mL respectively.

Each of the following compounds was synthesized and assayed using the procedures described above:
- 4-(1-azabicyclo[2.2.2]oct-3-ylamino)-3-(1H-benzimidazol-2-yl)-6-fluoro-1,7-naphthyridin-2(1H)-one;
- 4-(1-azabicyclo[2.2.2]oct-3-ylamino)-3-(1H-benzimidazol-2-yl)-6-chloro-1,7-naphthyridin-2(1H)-one;
- 3-benzimidazol-2-yl-4-hydroxyhydropyridino[3,4-b]pyridin-2-one;
- 4-hydroxy-3-(5-methylbenzimidazol-2-yl)hydropyridino[3,4-b]pyridin-2-one;
- 4-amino-3-benzimidazol-2-ylhydropyridino[3,4-b]pyridin-2-one;

4-amino-3-(5-methylbenzimidazol-2-yl)hydropyridino[3,4-b]pyridin-2-one;
4-amino-3-[5-(2-morpholin-4-ylethoxy)benzimidazol-2-yl]hydropyridino[3,4-b]pyridin-2-one;
[2-(4-amino-2-oxohydropyridino[3,4-b]pyridin-3-yl)benzimidazol-5-yl]-N,N-dimethylcarboxamide;
4-amino-3-(5-morpholin-4-ylbenzimidazol-2-yl)hydropyridino[3,4-b]pyridin-2-one;
4-amino-3-{5-[3-(dimethylamino)pyrrolidinyl]benzimidazol-2-yl}hydropyridino[3,4-b]pyridin-2-one;
4-amino-3-(3H-imidazo[4,5-b]pyridin-2-yl)-1,7-naphthyridin-2(1H)-one;
4-amino-3-[5-(4-methylpiperazin-1-yl)-1H-benzimidazol-2-yl]-1,7-naphthyridin-2(
4-amino-3-(5-morpholin-4-yl-1H-benzimidazol-2-yl)-1,6-naphthyridin-2(1H)-one;
4-amino-3-{5-[3-(dimethylamino)pyrrolidin-1-yl]-1H-benzimidazol-2-yl}-1,5-naphthyridin-2(1H)-one;
4-amino-3-[5-(4-methylpiperazin-1-yl)-1H-benzimidazol-2-yl]-1,5-naphthyridin-2(
3-(1H-benzimidazol-2-yl)-4-hydroxy-1,8-naphthyridin-2(1H)-one;
4-amino-5-(1H-benzimidazol-2-yl)-1,7-dihydro-6H-pyrazolo[3,4-b]pyridin-6-one;
4-amino-5-(1H-benzimidazol-2-yl)thieno[2,3-b]pyridin-6(7H)-one;
7-amino-6-(1H-benzimidazol-2-yl)-3,4-dihydro-5H-imidazo[4,5-b]pyridin-5-one; and
4-amino-5-(1H-benzimidazol-2-yl)-1-methyl-1,7-dihydro-6H-pyrazolo[3,4-b]pyridin-6-one.

Each of the above compounds displayed an $IC_{50}$ value of less than 10 μM with respect to VEGFR1, KDR, and bFGF.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the following claims.

---

What is claimed is:
1. A compound having the structure I, a tautomer of the compound, a pharmaceutically acceptable salt of the compound, or a pharmaceutically acceptable salt of the tautomer

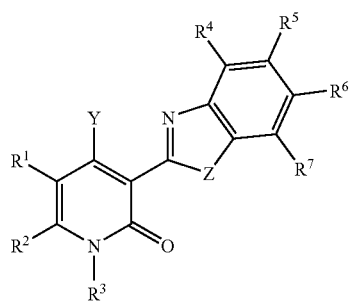

wherein,
Y is selected from the group consisting of —OH, —OR$^8$ groups, —SH, —SR$^9$ groups, —NR$^{10}$R$^{11}$ groups, —CN, —C(=O)—R$^{12}$ groups, substituted and unsubstituted alkyl groups, substituted and unsubstituted alkenyl groups, substituted and unsubstituted alkynyl groups, substituted and unsubstituted aralkyl groups, substituted and unsubstituted heterocyclylalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted heterocyclyl groups, substituted and unsubstituted aryl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;
Z is selected from the group consisting of O, S, and NR$^{13}$ groups;
R$^1$ and R$^2$ join to form a 6 membered substituted or unsubstituted ring comprising at least one O, N, or S atom;
R$^3$ and R$^{13}$ may be the same or different and are selected from the group consisting of H, —OH, substituted and unsubstituted alkoxy groups, substituted and unsubstituted alkyl groups, substituted and unsubstituted aryl groups, —C(=O)H, —C(=O)-alkyl groups, and —C(=O)-aryl groups;
R$^4$, R$^5$, R$^6$, and R$^7$ may be the same or different and are independently selected from the group consisting of H, Cl, Br, F, I, —NO$_2$, —CN, —OH, —OR$^{14}$ groups, —NR$^{15}$R$^{16}$ groups, —C(=O)R$^{17}$ groups, —SH, —SR$^{18}$ groups, —S(=O)R$^{19}$ groups, S(=O)$_2$R$^{20}$ groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted aminoalkyl groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;
R$^8$ is selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, and —C(=O)N(aryl)(heterocyclyl) groups;
R$^9$ and R$^{18}$ may be the same or different and are independently selected from the group consisting of substituted and unsubstituted alkyl groups, and substituted and unsubstituted aryl groups;
R$^{10}$ is selected from the group consisting of H, substituted and unsubstituted alkyl groups, substituted and unsubstituted aryl groups, and substituted and unsubstituted heterocyclyl groups;
R$^{11}$ is selected from the group consisting of H, substituted and unsubstituted alkyl groups, substituted and unsubstituted aryl groups, substituted and unsubstituted heterocyclyl groups, —OH, alkoxy groups, aryloxy groups, —NH$_2$, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R^{12}$ is selected from the group consisting of H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted and unsubstituted alkyl groups, substituted and unsubstituted aryl groups, —NH(heterocyclyl) groups, —N(heterocyclyl)$_2$ groups, —N(alkyl)(heterocyclyl) groups, and —N(aryl)(heterocyclyl) groups;

$R^{14}$ is selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)-heterocyclyl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)NH-heterocyclyl groups, —C(=O)N-(heterocyclyl)$_2$ groups, —C(=O)N(alkyl)(heterocyclyl) groups, —C(=O)N(aryl)(heterocyclyl) groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted and unsubstituted alkoxyalkyl groups, substituted and unsubstituted aryloxyalkyl groups, substituted and unsubstituted hydroxyalkyl groups, and substituted and unsubstituted heterocyclyloxyalkyl groups;

$R^{15}$ is selected from the group consisting of H, substituted and unsubstituted alkyl groups, substituted and unsubstituted aryl groups, and substituted and unsubstituted heterocyclyl groups;

$R^{16}$ is selected from the group consisting of H, substituted and unsubstituted alkyl groups, substituted and unsubstituted aryl groups, and substituted and unsubstituted heterocyclyl groups, —C(=O)H, —C(=O)-alkyl groups, —C(=O)-aryl groups, —C(=O)NH$_2$, —C(=O)NH (alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; and $R^{17}$, $R^{19}$, and $R^{20}$ may be the same or different and are independently selected from the group consisting of H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, —OH, substituted and unsubstituted alkoxy groups, substituted and unsubstituted heterocyclyl groups, substituted and unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups.

2. The compound according to claim 1, wherein Y is selected from the group consisting of —OH, —OR$^8$ groups, and —NR$^{10}$R$^{11}$ groups.

3. The compound according to claim 1, wherein Y is a —NR$^{10}$R$^{11}$ group.

4. The compound according to claim 1, wherein Z is an NR$^{13}$ group.

5. The compound according claim 1, wherein R$^4$ and R$^7$ are hydrogen and R$^5$ and R$^6$ are selected from the group consisting of hydrogen and alkyl groups having from 1 to 4 carbon atoms.

6. The compound according to claim 1, wherein R$^5$ or R$^6$ is an —OR$^{14}$ group and R$^{14}$ is an alkyl, aryl, heterocyclyl, or heterocyclylalkyl group.

7. The compound according to claim 1, wherein R$^5$ or R$^6$ is a —OCH$_2$(CH$_2$)$_q$(heterocyclyl) group and q is 0, 1, 2, 3, or 4.

8. The compound according to claim 1, wherein R$^{17}$ is selected from the group consisting of substituted and unsubstituted alkyl groups, substituted and unsubstituted aryl groups, —NH$_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, and N-containing heterocycles, wherein the N-containing heterocycles are bonded to the carbonyl carbon of the —C(=O)—R$^{17}$ group through either a nitrogen atom or a carbon atom in the rings of the N-containing heterocycles.

9. The compound according to claim 1, wherein one of R$^{10}$ or R$^{11}$ is H.

10. The compound according to claim 1, wherein R$^{10}$ and R$^{11}$ are both H.

11. The compound according to claim 10, wherein R$^1$ and R$^2$ join to form a substituted or unsubstituted 6 membered ring comprising at least one N atom.

12. The compound according to claim 11, wherein at least one of R$^5$ or R$^6$ is a substituted or unsubstituted heterocyclyl group.

13. The compound according to claim 11, wherein at least one of $R^5$ or $R^6$ is a substituted or unsubstituted heterocyclyl group selected from the group consisting of morpholine, piperazine, piperidine, 1,2,3-triazole, 1,2,4-triazole, tetrazole, pyrrolidine, pyrazole, pyrrole, thiomorpholine, homopiperazine, benzimidazole, oxazolidin-2-one, pyrrolidin-2-one, imidazole, isoxazole, oxazole, isothiazole, thiazole, thiophene, furan, pyran, tetrahydrothiophene, tetrahydrofuran, tetrahydropyran, and pyridine.

14. The compound according to claim 1, wherein $R^1$ and $R^2$ join to form a substituted or unsubstituted 6 membered ring comprising at least one N atom.

15. The compound according to claim 1, wherein at least one of $R^5$ or $R^6$ is a substituted or unsubstituted heterocyclyl group.

16. The compound according to claim 1, wherein at least one of $R^5$ or $R^6$ is a substituted or unsubstituted heterocyclyl group comprising at least one O or N atom.

17. The compound according to claim 1, wherein at least one of $R^5$ or $R^6$ is a substituted or unsubstituted heterocyclyl group selected from the group consisting of morpholine, piperazine, piperidine, 1,2,3-triazole, 1,2,4-triazole, tetrazole, pyrrolidine, pyrazole, pyrrole, thiomorpholine, homopiperazine, benzimidazole, oxazolidin-2-one, pyrrolidin-2-one, imidazole, isoxazole, oxazole, isothiazole, thiazole, thiophene, furan, pyran, tetrahydrothiophene, tetrahydrofuran, tetrahydropyran, and pyridine.

18. The compound according to claim 1, wherein Y is selected from the group consisting of from —N(CH$_3$)$_2$, —NH(CH$_3$), —NH(CH$_2$CH$_3$), —N(CH$_2$CH$_3$)$_2$, —NH(aryl) groups, —N(aryl)$_2$ groups, —NHNH$_2$, —NHN(CH$_3$)$_2$, —N(CH$_3$)NH(CH$_3$), —NH(CH$_2$)$_m$NH$_2$ groups, —NH(CH$_2$)$_m$ NH(alkyl) groups, —NH(CH$_2$)$_m$N(alkyl)$_2$ groups, —N(alkyl)(CH$_2$)$_m$NH$_2$ groups, —N(alkyl)(CH$_2$)$_m$NH(alkyl) groups, —N(alkyl)(CH$_2$)$_m$N(alkyl)$_2$ groups, —NH(CH$_2$)$_n$(heterocyclyl) groups, —N(alkyl)[(CH$_2$)$_n$(heterocyclyl)] groups, —NH(CH$_2$)$_m$OH groups, —NH(CH$_2$)$_m$OCH$_3$ groups, —NHCH$_2$CH(NH$_2$)CH(CH$_3$)$_2$, —NH(2-aminocyclohexyl), —NH(cyclohexyl), —NHOCH$_3$, —NH(N-morpholinyl), and —NH(quinuclidyl), wherein m is 2, 3, or 4 and n is 0, 1, 2, or 3.

19. A pharmaceutical formulation, comprising the compound according to claim 1 in combination with a pharmaceutically acceptable carrier.

* * * * *

UNITED STATES PATENT AND TRADEMARK OFFICE
CERTIFICATE OF CORRECTION

PATENT NO. : 7,138,409 B2
APPLICATION NO. : 10/823995
DATED : November 21, 2006
INVENTOR(S) : Paul A. Renhowe et al.

It is certified that error appears in the above-identified patent and that said Letters Patent is hereby corrected as shown below:

IN THE SPECIFICATION:

Column 11, Line 62: Delete "carboN(s) or hydrogeN(s)" and replace with --carbon(s) or hydrogen(s)--.

Column 13, Line 2: Delete "—C(H)$_2$C—C(CH$_3$)," and replace with -- —C(H)$_2$C≡C(CH$_3$), --.

Column 14, Line 9: Delete "0.3" and replace with --3--.

Column 33, Line 50: Delete "—N(aryl)$_2$ groups,".

Column 39, Line 39: Delete " 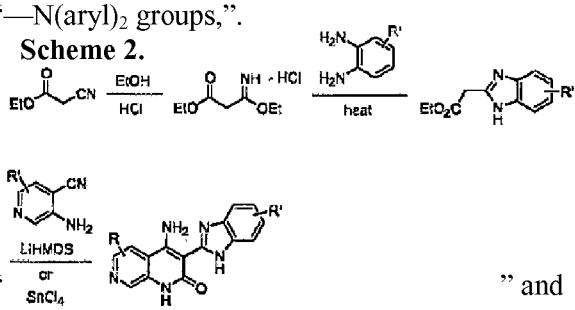 " and replace with -- 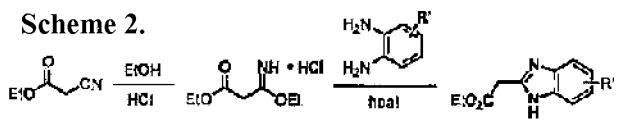 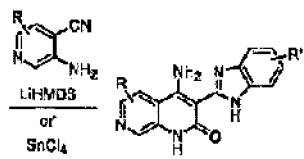 --.

Column 57, Line 14: Delete "2-yl]-1,7-naphthyridin-2(" and replace with --2-yl]-1,7-naphthyridin-2(1H)-one;--.

UNITED STATES PATENT AND TRADEMARK OFFICE
CERTIFICATE OF CORRECTION

PATENT NO. : 7,138,409 B2
APPLICATION NO. : 10/823995
DATED : November 21, 2006
INVENTOR(S) : Paul A. Renhowe et al.

It is certified that error appears in the above-identified patent and that said Letters Patent is hereby corrected as shown below:

Column 57, Line 20: Delete "2-yl]-1,5-naphthyridin-2(" and replace with --2-yl]-1,5-naphthyridin-2(1H)-one;--.

Signed and Sealed this

Twenty-fourth Day of April, 2007

JON W. DUDAS
*Director of the United States Patent and Trademark Office*